(12) United States Patent
Pickens

(10) Patent No.: US 6,716,212 B1
(45) Date of Patent: Apr. 6, 2004

(54) UNIVERSAL MODULAR EXTERNAL FIXATION SYSTEM

(76) Inventor: Tyrone Sam Pickens, 5901 E. Washington St., Apt. # 24, Indianapolis, IN (US) 46219

( * ) Notice: Subject to any disclaimer, the term of this patent is extended or adjusted under 35 U.S.C. 154(b) by 0 days.

(21) Appl. No.: 10/056,334

(22) Filed: Jan. 25, 2002

(51) Int. Cl.[7] .............................................. A61B 17/60
(52) U.S. Cl. ...................................................... 606/54
(58) Field of Search ............................. 606/53–59, 72, 606/73, 96, 97, 98, 105; 403/24, 53, 72; 604/264

(56) References Cited

U.S. PATENT DOCUMENTS

| | | | |
|---|---|---|---|
| 2,372,866 A | * 4/1945 | Tofflemire | 606/54 |
| 4,273,116 A | 6/1981 | Chiquet | |
| 4,450,835 A | * 5/1984 | Asnis et al. | 606/73 |
| 4,465,065 A | * 8/1984 | Gotfried | 606/65 |
| 4,535,763 A | * 8/1985 | Jaquet | 606/56 |
| 4,584,995 A | 4/1986 | Koeneman | |
| 4,600,000 A | * 7/1986 | Edwards | 606/54 |
| 4,628,922 A | * 12/1986 | Dewar | 606/56 |
| D303,577 S | 9/1989 | Hammer | |
| 5,152,280 A | * 10/1992 | Danieli | 606/54 |
| 5,263,498 A | * 11/1993 | Caspari et al. | 128/898 |
| 5,393,161 A | 2/1995 | Mata et al. | |
| 5,397,322 A | * 3/1995 | Campopiano | 606/57 |
| 5,437,667 A | 8/1995 | Papierski et al. | |
| 5,443,464 A | 8/1995 | Russell et al. | |
| 5,531,751 A | * 7/1996 | Schultheiss et al. | 606/96 |
| 5,690,633 A | * 11/1997 | Taylor et al. | 606/73 |
| 5,746,741 A | * 5/1998 | Kraus et al. | 606/54 |
| 5,797,908 A | * 8/1998 | Meyers et al. | 606/54 |
| 5,997,537 A | * 12/1999 | Walulik | 606/56 |
| 6,019,769 A | * 2/2000 | McCarthy et al. | 606/105 |
| 6,030,387 A | * 2/2000 | Ballier | 606/59 |
| 6,428,540 B1 | * 8/2002 | Claes et al. | 606/53 |
| 6,530,929 B1 | * 3/2003 | Justis et al. | 606/103 |
| 6,537,274 B1 | * 3/2003 | Katz | 606/56 |
| 2003/0065328 A1 | * 4/2003 | Shevtsov et al. | 606/54 |

* cited by examiner

Primary Examiner—Eduardo C. Robert
Assistant Examiner—David C Comstock

(57) ABSTRACT

A universal modular external fixation system for immobilizing bone fragments in long bone fractures. The universal modular external fixation system includes a frame assembly comprising a plurality of pins designed to be coupled to various portions of a fractured bone. The external sections of the pins are fixated to a variety of different coupling devices designed to attach to a series of connecting bars along the length of the fractured bone. A plurality of connecting members interconnect the connecting bars thereby securing the pins and thus the bone sections to aid in proper healing of the fracture(s).

28 Claims, 18 Drawing Sheets

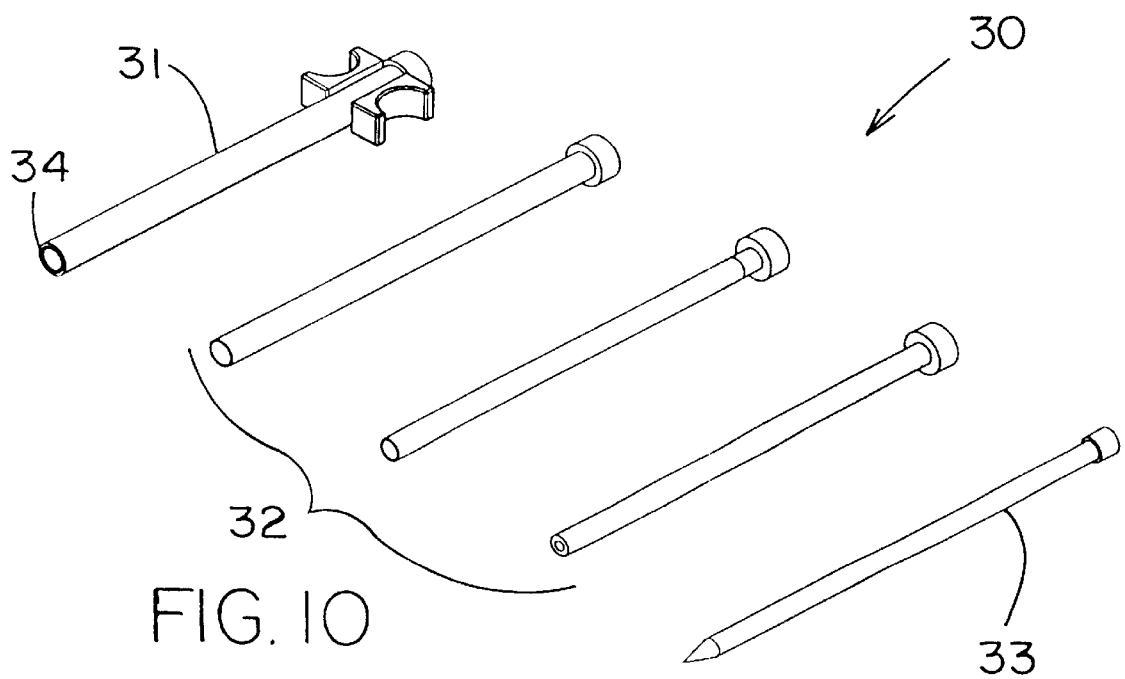

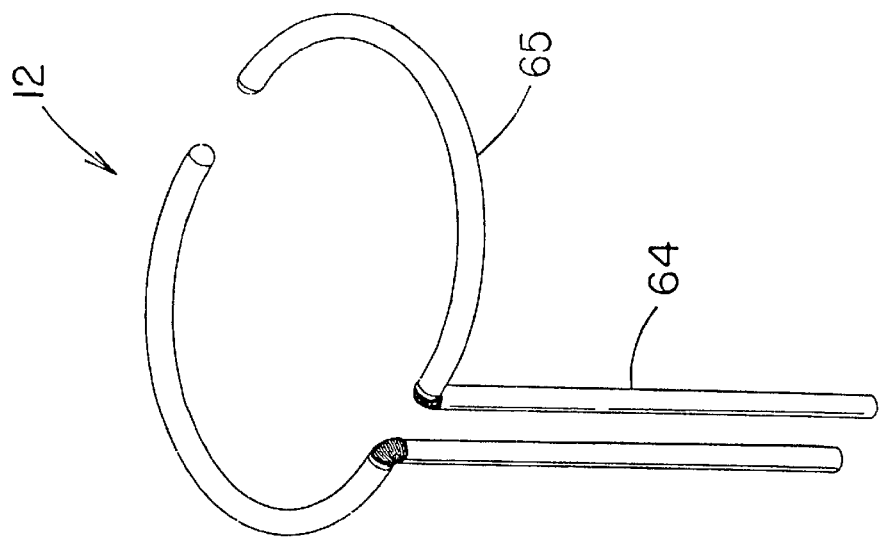
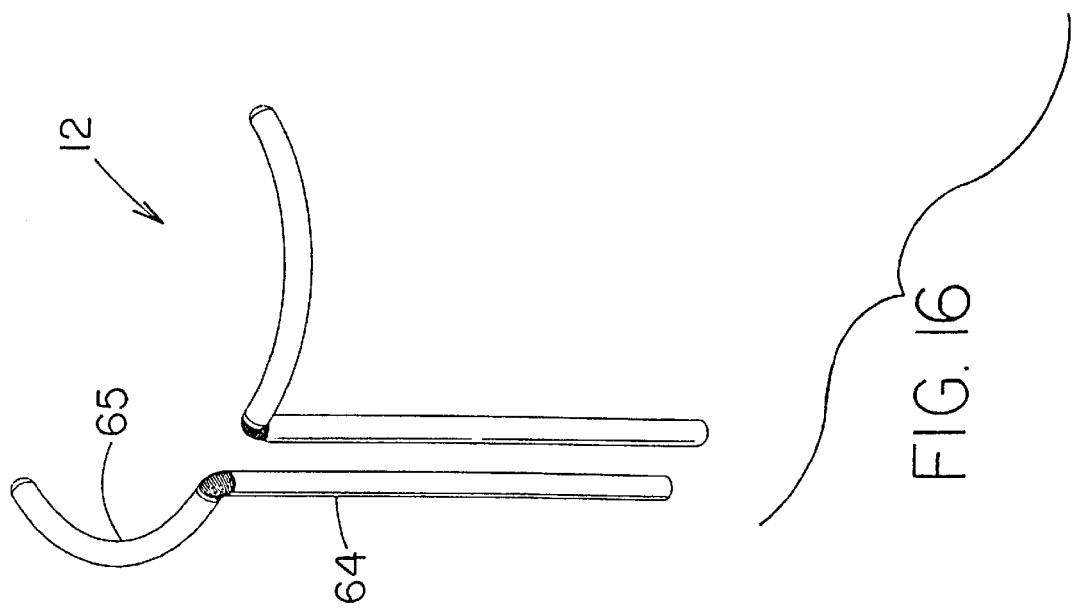
FIG. 16

UNIVERSAL MODULAR EXTERNAL FIXATION SYSTEM

BACKGROUND OF THE INVENTION

1. Field of the Invention

The present invention relates to external fixation systems and more particularly pertains to a new universal modular external fixation system for immobilizing bone fragments in long bone fractures.

2. Description of the Prior Art

The use of external fixation systems is known in the prior art. More specifically, external fixation systems heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,437,667; U.S. Pat. No. 4,584,995; U.S. Pat. No. 5,393,161; U.S. Pat. No. 5,443,464; U.S. Pat. No. 4,273,116; and U.S. Pat. No. Des. 303,577.

While these devices fulfill their respective, particular objectives and requirements, the aforementioned patents do not disclose a new universal modular external fixation system. The inventive device includes a frame assembly comprising a plurality of pins designed to be coupled to various portions of a fractured bone. The external sections of the pins are fixated to a variety of different coupling devices designed to attach to a series of connecting bars along the length of the fractured bone. A plurality of connecting members interconnect the connecting bars thereby securing the pins and thus the bone sections to aid in proper healing of the fracture(s).

In these respects, the universal modular external fixation system according to the present invention substantially departs from the conventional concepts and designs of the prior art, and in so doing provides an apparatus primarily developed for the purpose of immobilizing bone fragments in long bone fractures.

SUMMARY OF THE INVENTION

In view of the foregoing disadvantages inherent in the known types of external fixation systems now present in the prior art, the present invention provides a new universal modular external fixation system construction wherein the same can be utilized for immobilizing bone fragments in long bone fractures.

The general purpose of the present invention, which will be described subsequently in greater detail, is to provide a new universal modular external fixation system apparatus and method which has many of the advantages of the external fixation systems mentioned heretofore and many novel features that result in a new universal modular external fixation system which is not anticipated, rendered obvious, suggested, or even implied by any of the prior art external fixation systems, either alone or in any combination thereof.

To attain this, the present invention generally comprises a frame assembly comprising a plurality of pins designed to be coupled to various portions of a fractured bone. The external sections of the pins are fixated to a variety of different coupling devices designed to attach to a series of connecting bars along the length of the fractured bone. A plurality of connecting members interconnect the connecting bars thereby securing the pins and thus the bone sections to aid in proper healing of the fracture(s).

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new universal modular external fixation system apparatus and method which has many of the advantages of the external fixation systems mentioned heretofore and many novel features that result in a new universal modular external fixation system which is not anticipated, rendered obvious, suggested, or even implied by any of the prior art external fixation systems, either alone or in any combination thereof.

It is another object of the present invention to provide a new universal modular external fixation system which may be easily and efficiently manufactured and marketed.

It is a further object of the present invention to provide a new universal modular external fixation system which is of a durable and reliable construction.

An even further object of the present invention is to provide a new universal modular external fixation system which is susceptible of a low cost of manufacture with regard to both materials and labor, and which accordingly is then susceptible of low prices of sale to the consuming public, thereby making such universal modular external fixation system economically available to the buying public.

Still yet another object of the present invention is to provide a new universal modular external fixation system which provides in the apparatuses and methods of the prior art some of[]the advantages thereof, while simultaneously overcoming some of the disadvantages normally associated therewith.

Still another object of the present invention is to provide a new universal modular external fixation system for immobilizing bone fragments in long bone fractures.

Yet another object of the present invention is to provide a new universal modular external fixation system which includes a frame assembly comprising a plurality of pins designed to be coupled to various portions of a fractured bone. The external sections of the pins are fixated to a variety of different coupling devices designed to attach to a series of connecting bars along the length of the fractured bone. A plurality of connecting members interconnect the connecting bars thereby securing the pins and thus the bone sections to aid in proper healing of the fracture(s).

Still yet another object of the present invention is to provide a new universal modular external fixation system that can be utilized on a wide variety of bone fractures on various portions of the body.

Even still another object of the present invention is to provide a new universal modular external fixation system that utilizes unique connecting bars, coupling devices, and pins to accomplish in one system what would normally require several devices or methods.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 9 is a perspective view guide holder of the present invention.

FIG. 10 is a perspective view of different sized drill guides of the present invention.

FIG. 11 is a perspective view of a trocar of the present invention.

FIG. 16 is a perspective view of semi-circular connecting bars of the present invention.

DESCRIPTION OF THE PREFERRED EMBODIMENT

Figure 1:
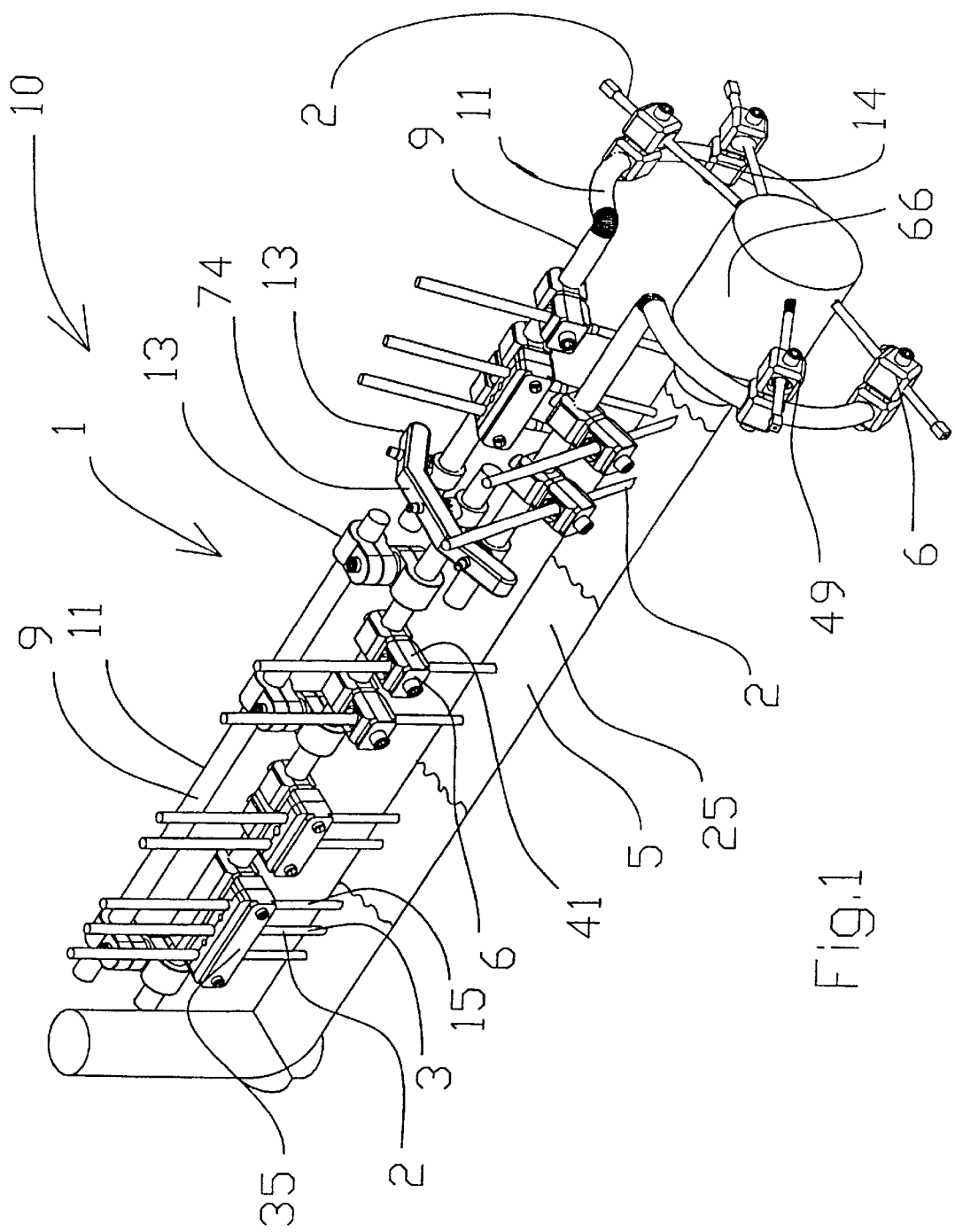
FIG. 1 is a perspective view of a new universal modular external fixation system according to the present invention.
Figure 2:
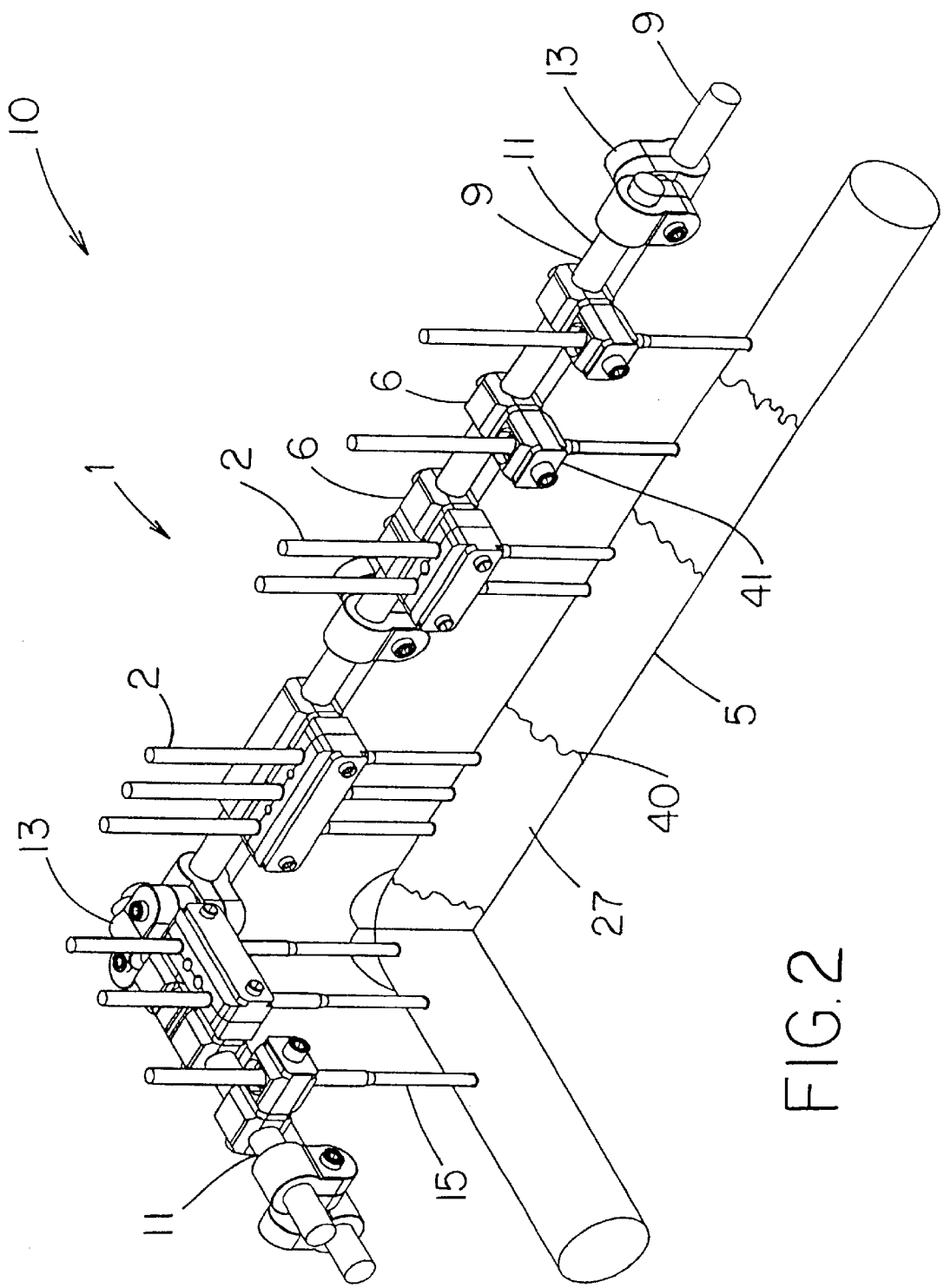
FIG. 2 is a perspective view of the present invention being utilized to immobilize the ankle and foot.
Figure 3:
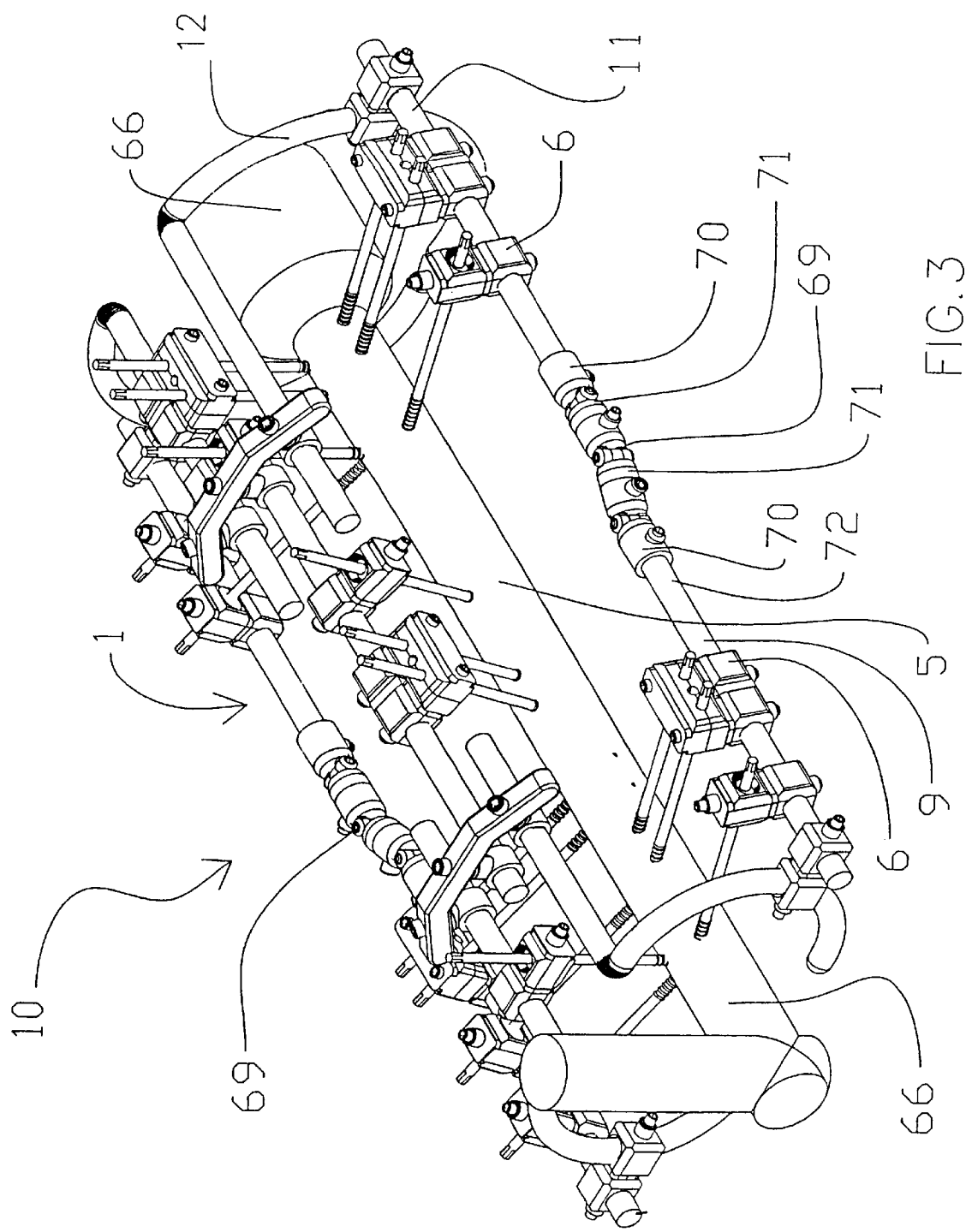
FIG. 3 is a perspective view of the present invention utilizing offset connecting members.
Figure 4:
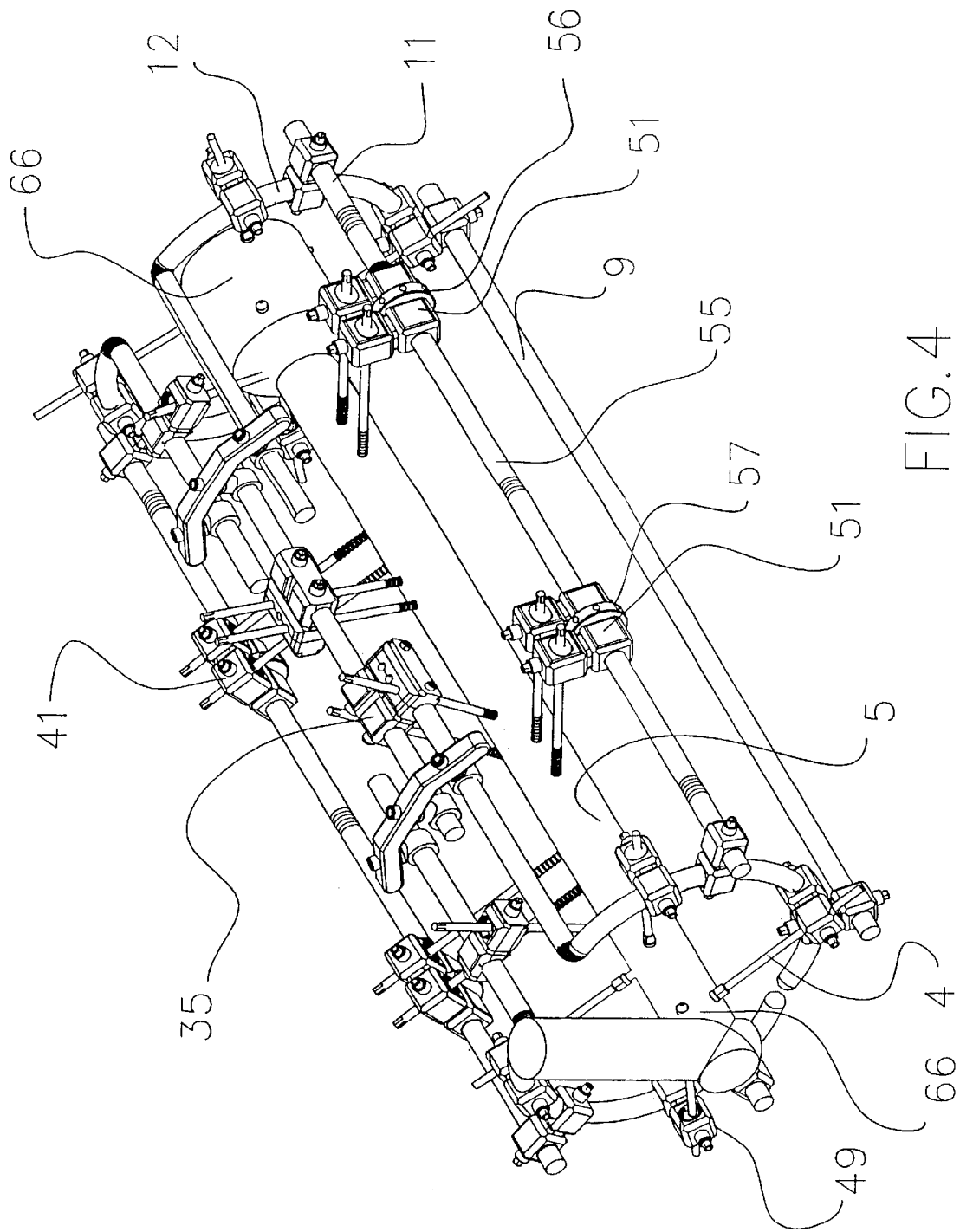
FIG. 4 is a perspective view of the present invention utilizing traction/distraction couplers.
Figure 5:
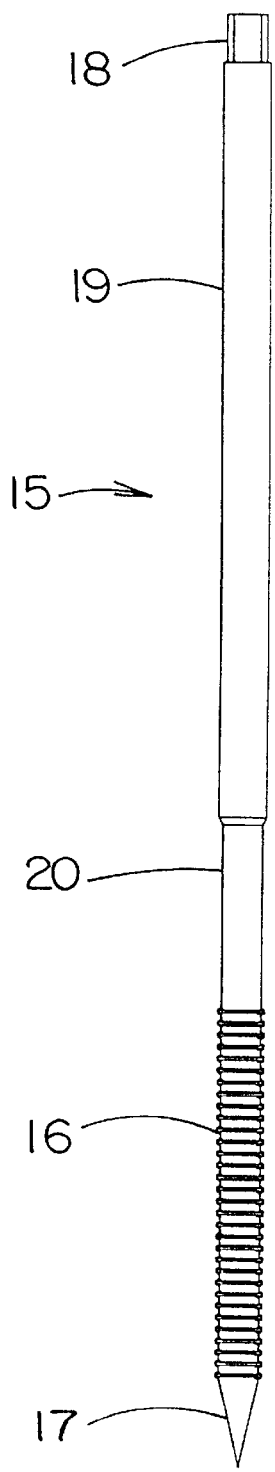
FIG. 5 is a side view of a step down fixation pin of the present invention.
Figure 6:
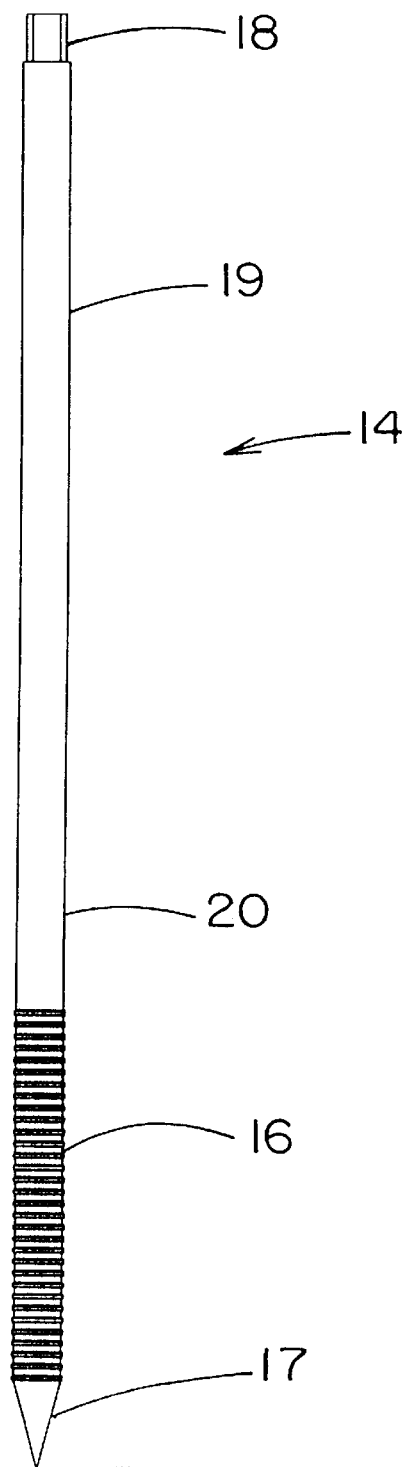
FIG. 6 is a side view of a standard fixation pin of the present invention.
Figure 7A:
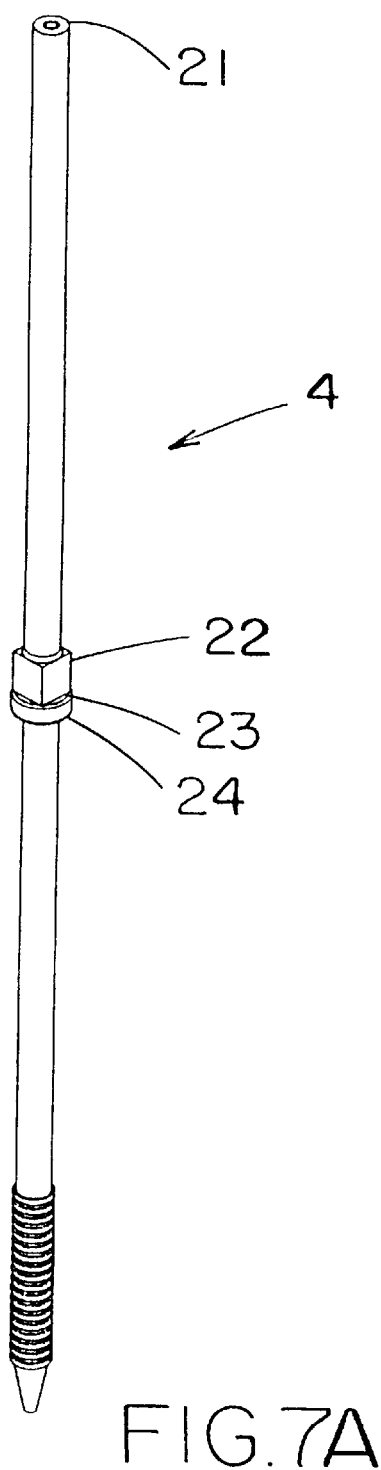
FIG. 7A is a perspective view of a compression pin of the present invention.
Figure 8:
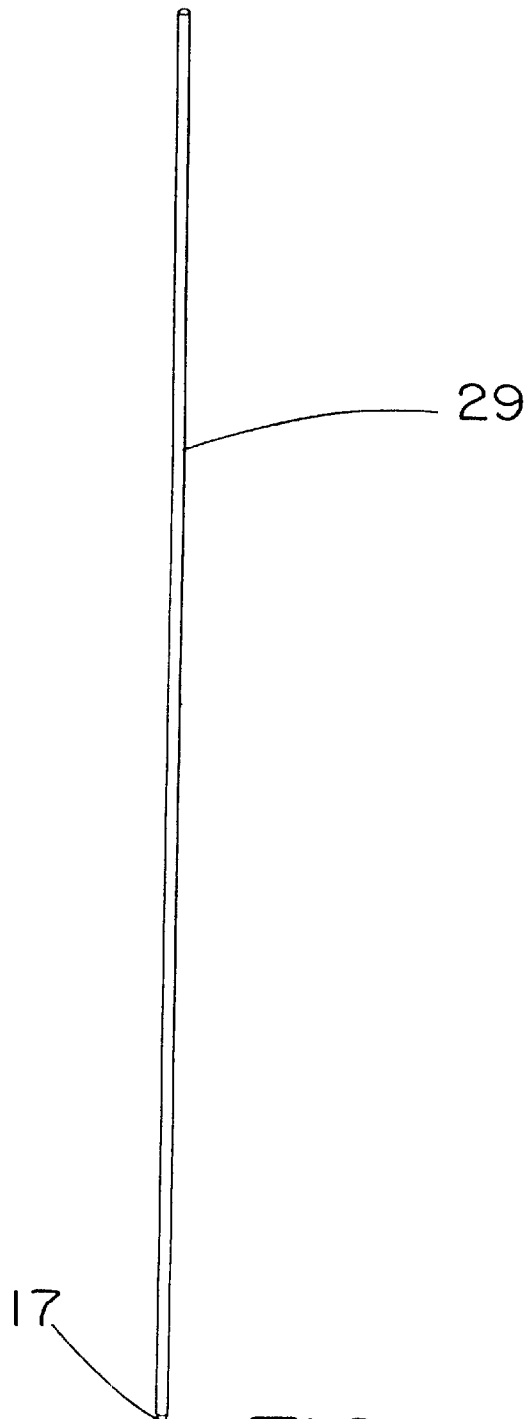
FIG. 8 is a perspective view the guide wire of the present invention.
Figure 7B:
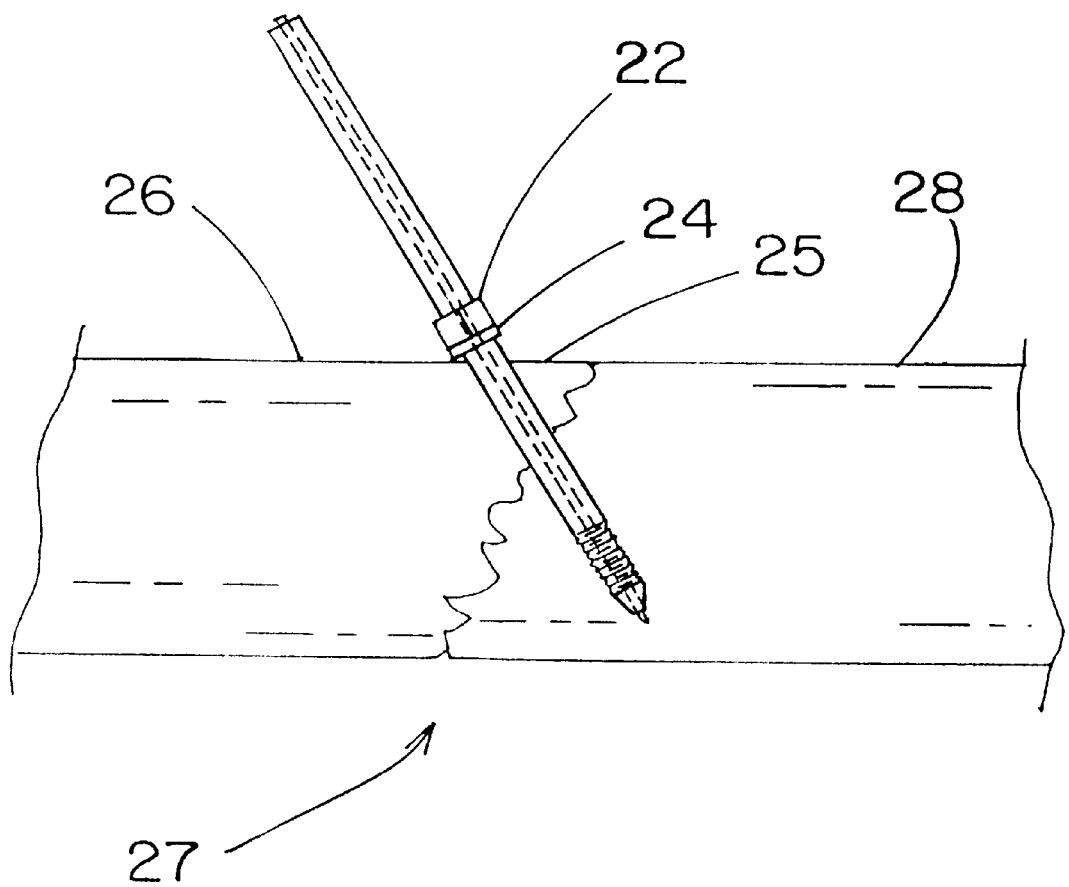
FIG. 7B is a perspective view of a compression pin of the present invention inserted into the bone.
Figure 12:
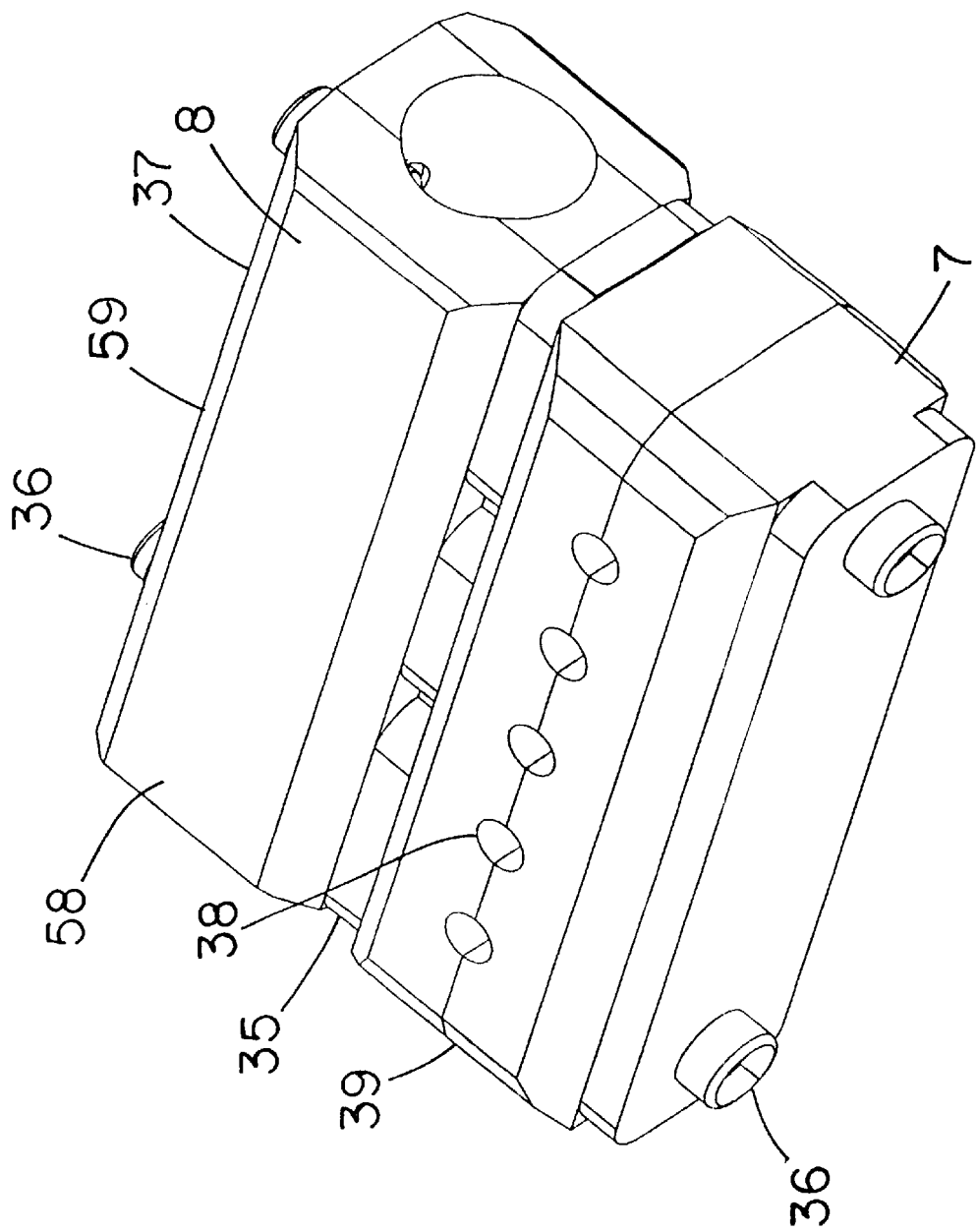
FIG. 12 is a perspective view of a multi-pin fixed coupler of the present invention.
Figure 13:
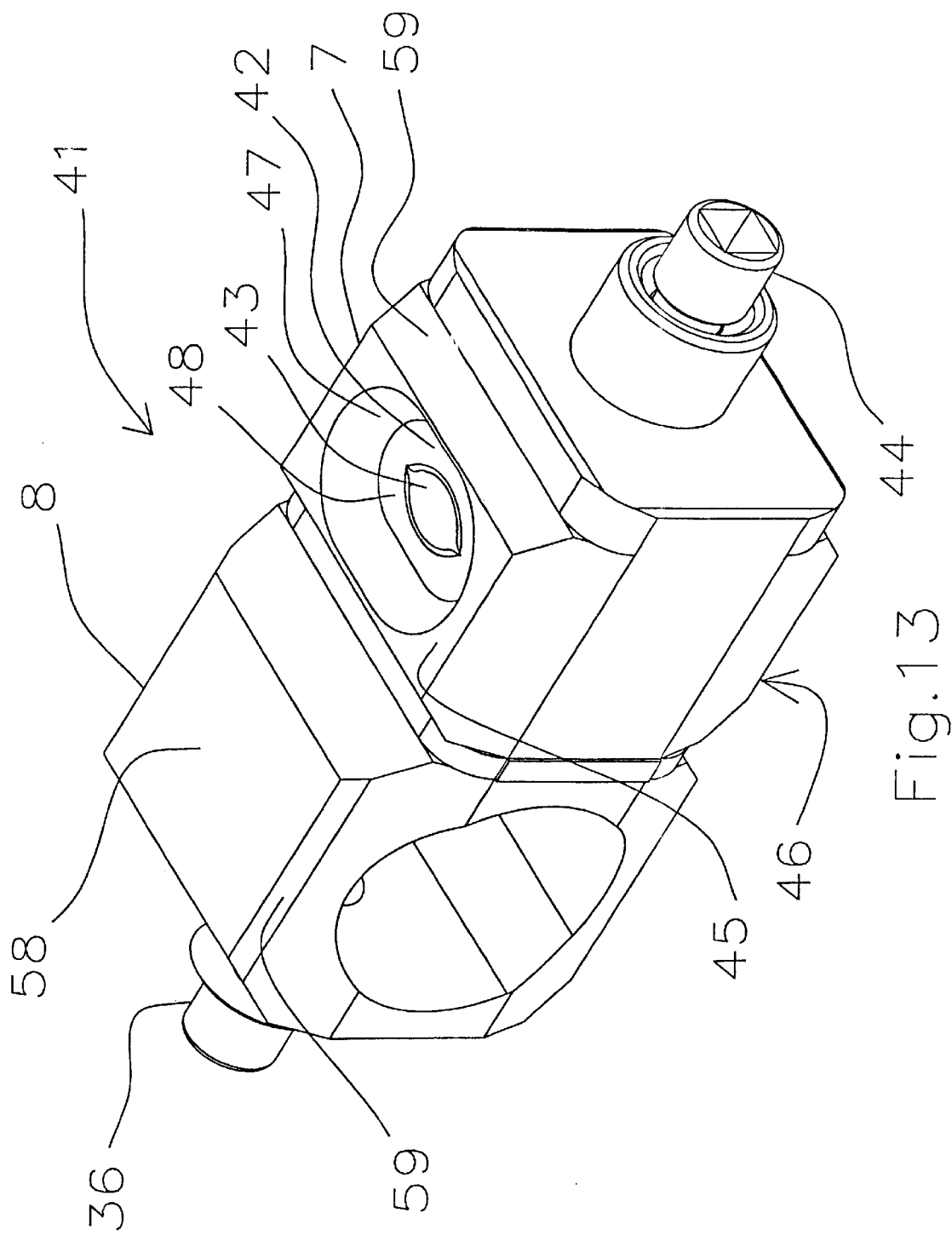
FIG. 13 is a perspective view a single axis pivotal coupler of the present invention.
Figure 14:
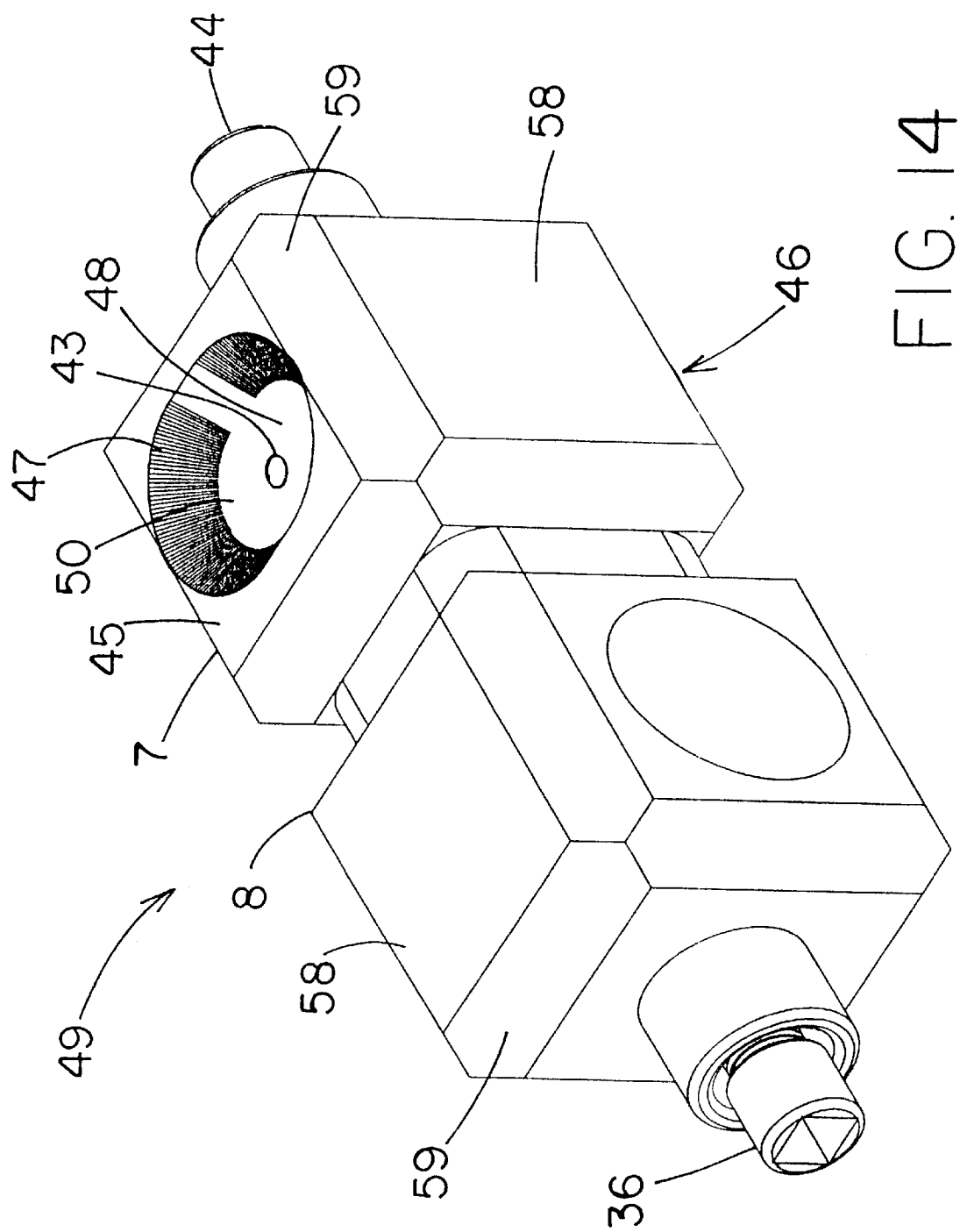
FIG. 14 is a perspective view a multi-axis pivotal coupler of the present invention.
Figure 15:
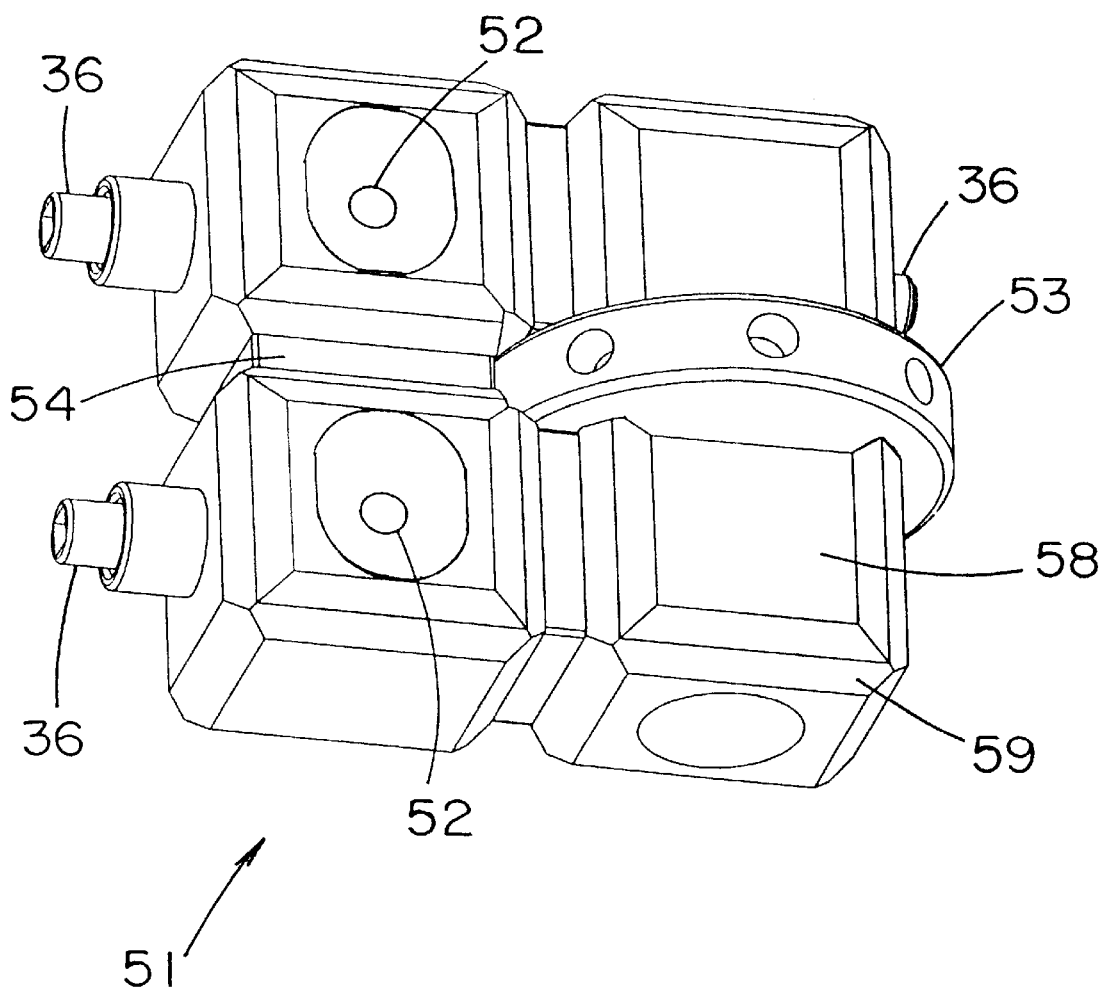
FIG. 15 is a perspective view a traction/distraction coupler of the present invention.
Figure 17:
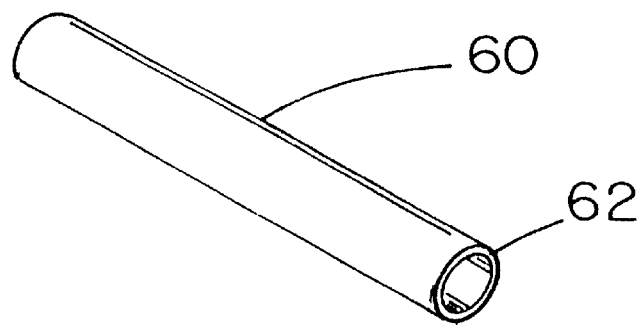
FIG. 17 is a perspective view of a standard connecting bar of the present invention.
Figure 18:
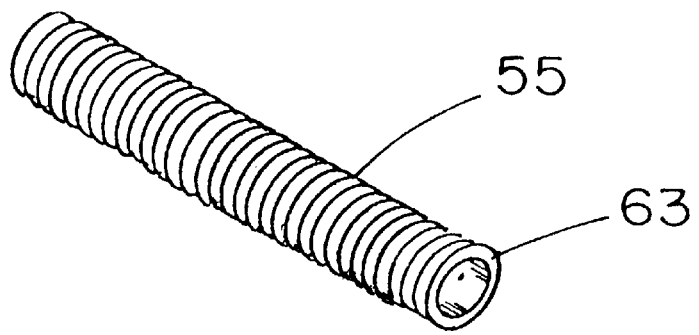
FIG. 18 is a perspective view of a threaded connecting bar of the present invention.
Figure 19:
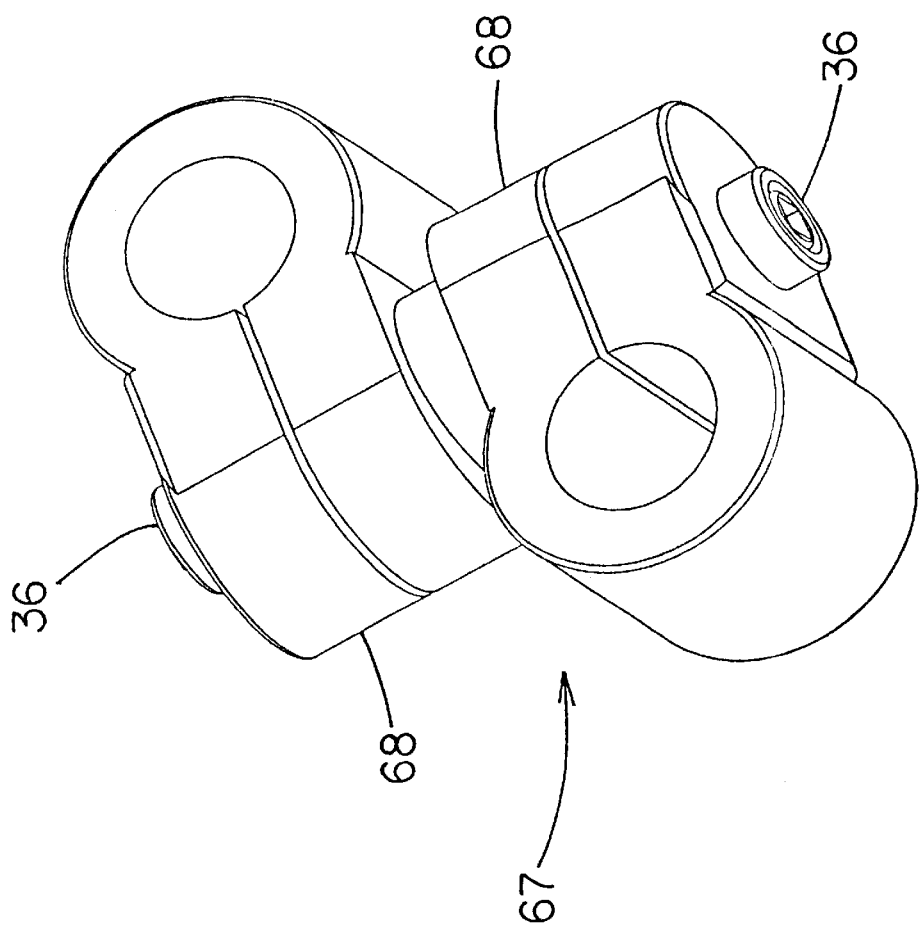
FIG. 19 is a perspective view of a standard connecting member of the present invention.
Figure 20:
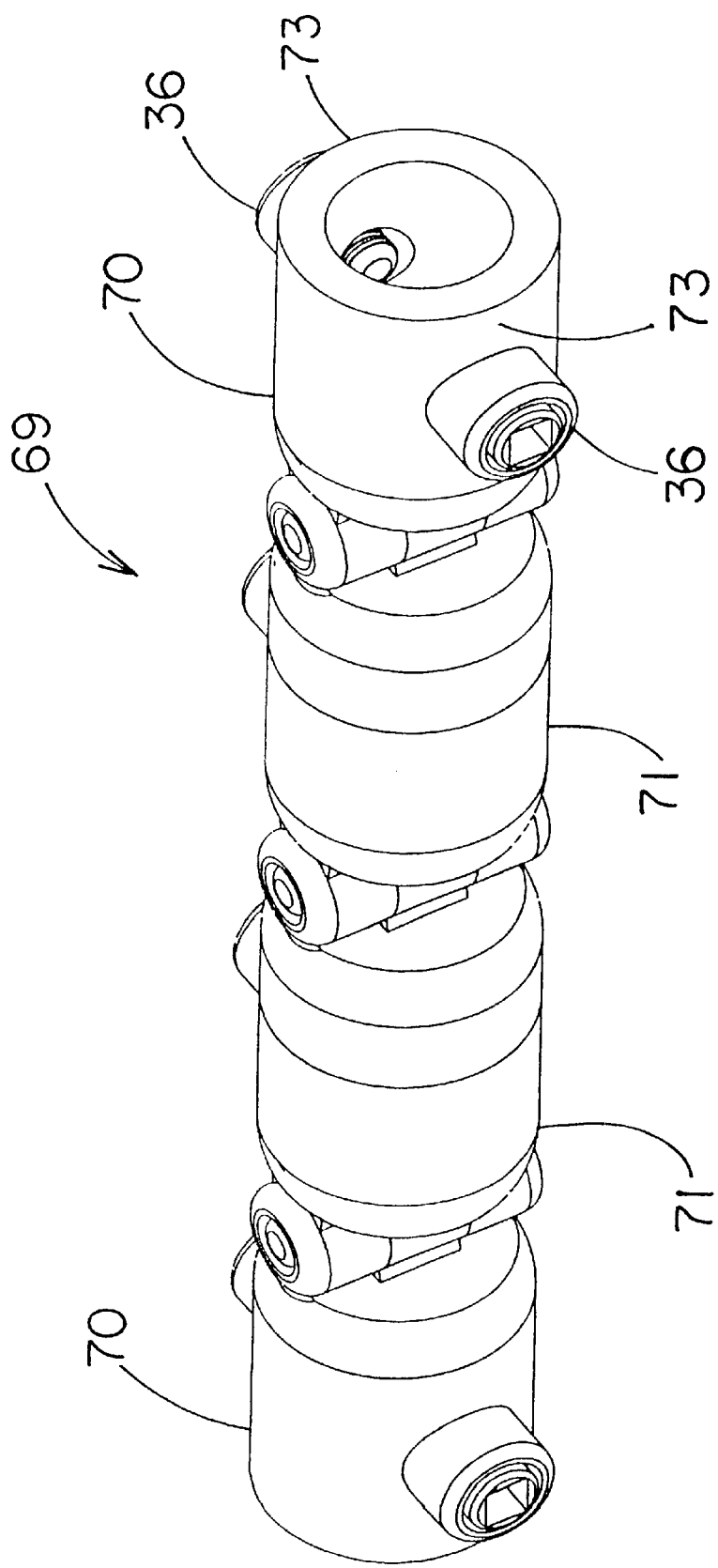
FIG. 20 is a perspective view of an offset connector of the present invention.
Figure 21:
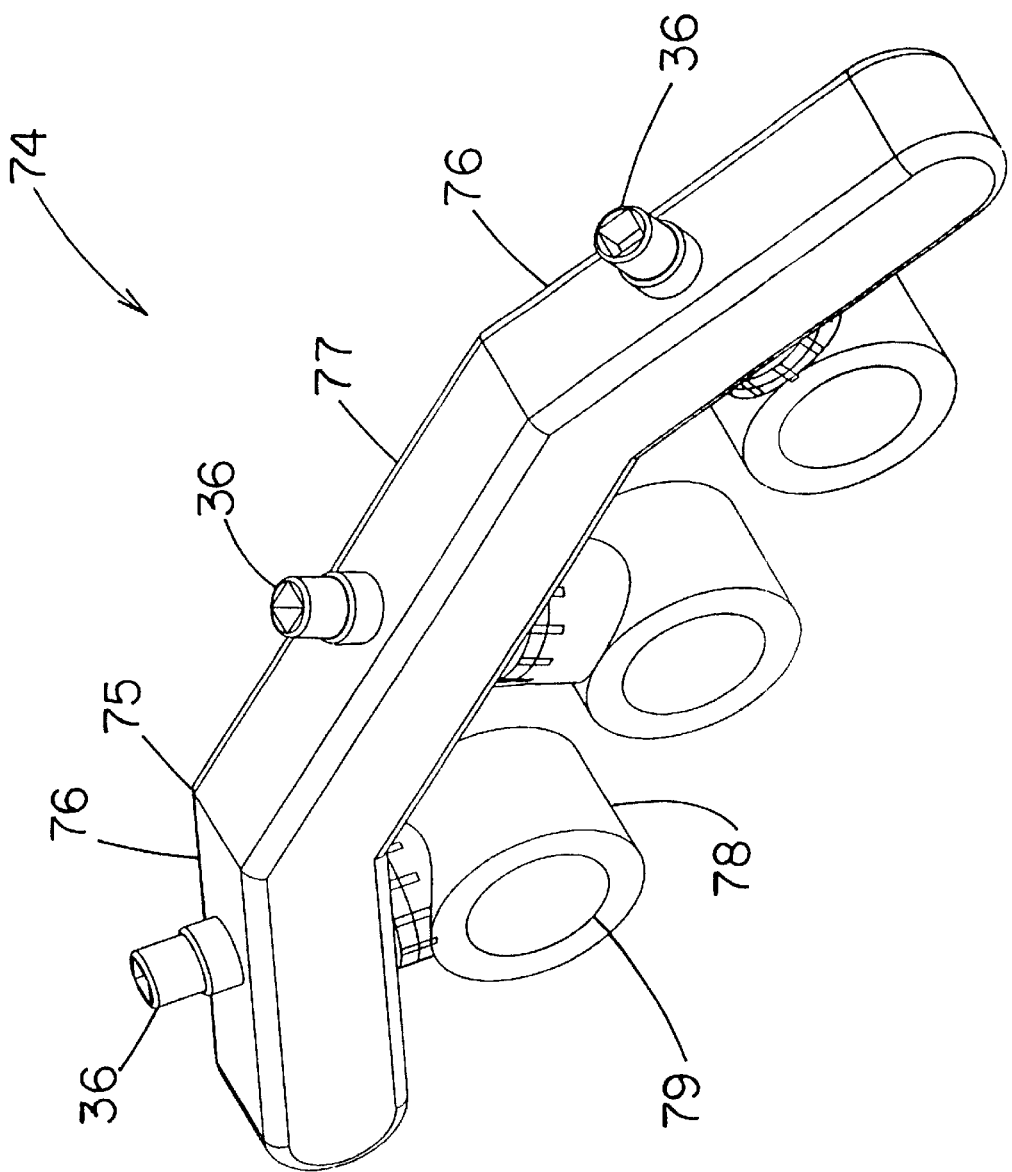
FIG. 21 is a perspective view an angular connector of the present invention.
Figure 22:
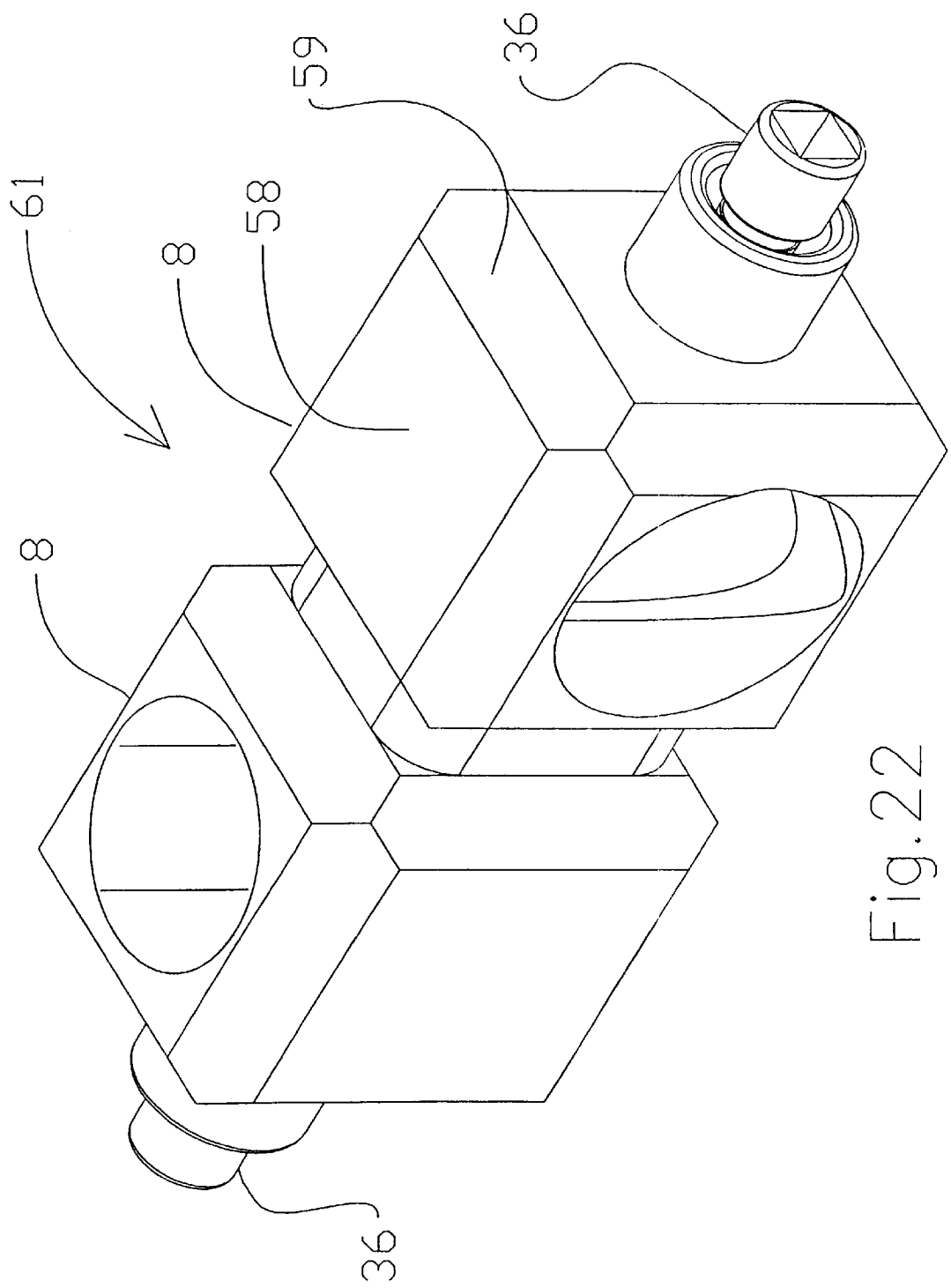
FIG. 22 is a perspective view of the present invention.

With reference now to the drawings, and in particular to FIGS. 1 through 22 thereof, a new universal modular external fixation system embodying the principles and concepts of the present invention and generally designated by the reference numeral 10 will be described.

As best illustrated in FIGS. 1 through 21, the universal modular external fixation system 10 generally comprises a frame assembly 1. The frame assembly 1 has a plurality of pins 2. The pins 2 comprise a plurality of fixation pins 3 and compression pins 4. The pins 2 are designed for being threadably couplable to a bone 5 for the purpose of rendering the bone 5 immobile.

The frame assembly 1 includes a plurality of couplers 6. The couplers 6 comprise a pin section 7 and a bar section 8. The pin section 7 is selectively couplable to the pins 2 such that the pin section 7 is designed for holding the pins 2 in a fixed position relative to the frame assembly 1.

The frame assembly 1 includes a plurality of connecting bars 9. The connecting bars 9 comprise straight connecting bars 11 and semi-circular connecting bars 12. The connecting bars 9 are slidable through the bar section 8 of the couplers 6. The connecting bars 9 are designed for allowing a user to position the couplers 6 along the connecting bars 9 such that the couplers 6 are selectively couplable to the pins 2 when the pins 2 are positioned in the bones 5.

The frame assembly 1 includes a plurality of connecting members 13. The connecting members 13 are selectively couplable to the connecting bars 9. The connecting members 13 are designed for rigidly securing a plurality of the connecting bars 9 together thereby completely immobilizing all of the pins 2 coupled to the bones 5 for the duration of the healing process.

The plurality of fixation pins 3 of the frame assembly 1 comprises a standard fixation pin 14 and a step down fixation pin 15. Each of the fixation pins 14, 15 has a threaded portion 16. The threaded portion 16 of the fixation pins 14, 15 is located proximate a point end 17 of the fixation pins 3. The threaded portion 16 is designed for being screwed into the bone 5.

Each of the fixation pins 3 has a tool end. The tool end is designed for allowing the user to utilize a tool to turn the fixation pin for the purpose of inserting or extracting the fixation pin to and from the bone 5.

Each of the fixation pins 3 has a coupling portion 19 and an insertion portion 20. The coupling portions 19 of the fixation pins 3 have equal diameters. A diameter of the coupling portion 19 of the standard fixation pin 14 is equal to a diameter of the insertion portion 20 of the standard fixation pin 14, whereas a diameter of the insertion portion 20 of the step down fixation pin 15 is less than a diameter of the coupling portion 19 of the step down fixation pin 15 thereby making fixation pins 14, 15 having different insertion diameters both selectively couplable to one of the couplers 6.

The compression pin 4 of the frame assembly 1 is a substantially elongate tubular member 21. The compression pin 4 has the threaded portion 16 and the coupling portion 19. The compression pin 4 has a tool portion 22 positioned proximate a medial portion 23 of the compression pin 4. The tool portion 22 is designed for allowing the user to utilize a tool to turn the compression pin 4 for the purpose of inserting or extracting the compression pin 4 from the bone 5.

The compression pin 4 has a head portion 24. The head portion 24 is located adjacent the tool portion 22. The head portion 24 is designed for abutting an outer surface 25 of the fractured bone 27 when the threaded portion 16 of the compression pin 4 passes completely through a first part of a fractured bone 26 and is securely coupled to a second part of the fractured bone 27. The compression pin 4 is designed for biasing the first and second parts of the bone 26, 28 together until properly healed.

The compression pin 4 includes a guide wire 29. The guide wire 29 is insertable into the compression pin 4 such that the guide wire 29 protrudes outwardly from the point end 17 of the compression pin 4. The guide wire 29 is positioned in the bone 5 prior to screwing in the compression pin 4 such that the guide wire 29 is designed for predetermining a desired angle and location of the compression pin 4 by viewing x-rays with the guide wire 29 inserted thereby assuring proper placement of the compression pin 4 in the fractured bone 27.

A plurality of the compression pins 4 comprises a plurality of lengths of the insertion portions 20 for the purpose of matching a particular compression pin 4 to a specific fracture 40 requirement.

The frame assembly 1 includes a drill guide assembly 30. The drill guide assembly 30 comprises a guide holder 31, a plurality of drill guides 32, and a trocar 33. The trocar 33 is insertable into the guide holder 31 such that the trocar 33 protrudes outwardly from a bottom end 34 of the guide holder 31 thereby puncturing muscle covering the bone 5. The trocar 33 is then removed and one of the plurality of drill guides 32 is inserted into the guide holder 31. The drill guides 32 are designed for guiding various sized drill bits to ensure the uniformity of the hole being drilled into the bone 5 thereby assuring proper placement of the fixation pins 3.

The plurality of the couplers 6 of the frame assembly 1 includes a multi-pin fixed coupler 35. The bar section 8 of the multi-pin fixed coupler 35 has a plurality of securing members 36. The securing members 36 are positioned on a bar end 37 of the multi-pin fixed coupler 35. The securing members 36 are designed for contacting the connecting bar 9 thereby allowing a user to selectively fixate the multi-pin fixed coupler 35 onto the connecting bar 9 in a desired position.

The pin section 7 of the multi-pin fixed coupler 35 has a plurality of fixation pin apertures 38. The apertures 38 are formed by mating sectional portions 39 of the pin section 7 of the multi-pin fixed coupler 35. A diameter of the fixation pins 3 is greater than a diameter of the apertures 38 such that the fixation pins 3 are insertable into the apertures 38 when the sectional portions 39 are parted.

The apertures 38 are designed for securing the fixation pins 3 when a plurality of the securing members 36 of the pin section 7 are biased inwardly thus forcing the sectional portions 39 together. The diameter of the apertures 38 then decreases thereby securing the fixation pins 3 to the pin section 7 of the multi-pin fixed coupler 35.

The frame assembly 1 includes a plurality of the multi-pin fixed couplers 35. Each of the multi-pin fixed couplers 35 has a different number of pin apertures 38. The apertures 38 are aligned substantially parallel to the connecting bars 9 thereby allowing the user to space the fixation pins 3 as needed along the bone 5 for the purpose of immobilizing particular parts of the bone 5 for proper healing of the fracture 40.

The plurality of the couplers 6 of the frame assembly 1 includes a single axis pivotal coupler 41. The pin section 7 of the single axis pivotal coupler 41 has a pivotal pin member 42. The pivotal pin member 42 has a bore 43 therethrough. The bore 43 is designed for receiving one of the fixation pins 3. The pivotal pin member 42 is positioned within the pin section 7 of the single axis pivotal coupler 41.

The pivotal pin member 42 is pivotable thirty degrees either side of a central axis of the coupler 41 in a plane parallel to a vertical plane of a longitudinal axis of the connecting bars 9. The central axis is substantially perpendicular to a longitudinal axis of the coupler 41. The central axis is substantially perpendicular to, the longitudinal axis of the connecting bar 9 thereby allowing the user to position the fixation pin 3 at various angles with respect to the connecting bar 9 as needed.

A clamping member 44 of the pin section 7 is biased inwardly contacting the pivotal pin member 42 thereby securing the pivotal pin member 42 in a fixed position.

The pivotal pin member 42 of the single axis pivotal coupler 41 is collapsible when the clamping member 44 secures the pivotal pin member 42. A diameter of the bore 43 of the pivotal pin member 42 is decreased upon the securing of the pivotal pin member 42 by the clamping member 44 maintaining a position of one of the pins 2 in the bore 43.

Upper and lower surfaces 45, 46 of the pin section 7 of the single axis pivotal coupler 41 have an inner edge portion 47. The inner edge portion 47 is beveled outwardly from an exterior surface 48 of the pivotal pin member 42 thereby allowing the fixation pin to fully pivot the designated angular range of the pivotal pin member 42.

The bar section 8 of the single axis pivotal coupler 41 has a securing member such that the bar section 8 is designed for being selectively couplable to one of the connecting bars 9.

The plurality of the couplers 6 of the frame assembly 1 includes a multi-axis pivotal coupler 49. The pin section 7 of the multi-axis pivotal coupler 49 has a multi-axis pin member 50. The multi-axis pin member 50 has a bore 43 throughout. The bore 43 is designed for receiving one of the pins 2. The multi-axis pin member 50 is positioned within the pin section 7 of the multi-axis pivotal coupler 49. The multi-axis pin member 50 is pivotable thirty degrees about a central axis wherein the central axis is substantially perpendicular to a longitudinal axis of the coupler 49 thereby allowing the user to position the pins 2 at various angles with respect to the connecting bars 9 as required.

A clamping member 44 of the pin section 7 is biased inwardly contacting the multi-axis pin member 50 thereby securing the multi-axis pin member 50 in a fixed position.

The multi-axis pin member 50 of the multi-axis pivotal coupler 49 is collapsible when the clamping member 44 secures the pivotal pin member 42. A diameter of the bore 43 of the multi-axis pin member 50 is decreased upon the securing of the multi-axis pin member 50 by the clamping member 44 thereby maintaining a position of one of the pins 2 in the bore 43.

Upper and lower surfaces 45, 46 of the pin section 7 of the multi-axis pivotal coupler 49 have an inner edge portion 47. The inner edge portion 47 is beveled outwardly from an exterior surface 48 of the multi-axis pin member 50 thereby allowing the fixation pin to fully pivot the designated angular range of the multi-axis pin member 50.

The bar section 8 of the multi-axis pivotal coupler 49 is designed for receiving the semi-circular connecting bars 12. The bar section 8 has a securing member 36 such that the bar section 8 is designed for being selectively couplable to one of the semicircular connecting bars 12.

The plurality of the couplers 6 of the frame assembly 1 includes a traction/distraction coupler 51. The pin section 7 of the traction/distraction coupler 51 has a plurality of pin receiving holes 52. The pin receiving holes 52 are aligned along a longitudinal axis of the connecting bar 9.

The pin section 7 has a plurality of securing members 36 such that the pins 2 are selectively couplable to the pin section 7 when the securing members 36 are biased inwardly towards the pins 2.

The bar section 8 of the traction/distraction coupler 51 has a traction/distraction member 53. The traction/distraction member 53 is positioned proximate a middle section 54 of the traction/distraction coupler 51. The traction/distraction member 53 is threadably couplable to a threaded connecting bar 55. The traction/distraction member 53 is rotatable about a longitudinal axis of the threaded connecting bar 55 such that rotation of the traction/distraction member 53 biases the traction/distraction coupler 51 longitudinally along the threaded connecting bar 55.

The bar section 8 of the traction/distraction coupler 51 has a securing member 36. The securing member 36 is designed for contacting the threaded connecting bar 55 for the purpose of preventing rotation with respect to the traction/distraction coupler 51 when a pair of traction/distraction couplers 51 are coupled to the threaded rod and are utilized to bias bones 5 on either side of the fracture 40 as required.

A first of the traction/distraction couplers 56 is secured to the threaded connecting bar 55. A second of the traction/distraction couplers 57 is biased along the threaded connecting bar 55 by rotation of the traction/distraction member 53 when the pins 2 are secured to either side of the fracture 40.

All of the couplers 6 have smooth surfaces 58 and beveled edges 59 thereby allowing a user to grasp the couplers 6 when the user is wearing latex gloves and has a substantial amount of blood and fluid on the gloves making them slippery.

The straight connecting bars 11 of the connecting bars 9 includes standard connecting bars 60 and the threaded connecting bars 55. The standard connecting bars 60 comprise smooth tubular members 62 of various predetermined lengths. The standard connecting bars 60 are designed for receiving all of the couplers 6 except the traction/distraction couplers 51.

The threaded connecting bars 55 comprise threaded tubular members 63 of various predetermined lengths. The threaded connecting bars 55 are designed for receiving a plurality of traction/distraction couplers 51.

The semi-circular connecting bars 12 comprise a straight portion 64 and a curved portion 65. The portions are fixedly coupled such that a plane in which the curved portion 65 lies is substantially perpendicular to a longitudinal axis of the straight portion 64.

The semi-circular connecting bars 12 have a plurality of different length straight portions 64 in conjunction with a plurality of curved portions 65 having different radii.

The curved portions 65 of the semi-circular connecting bars 12 are designed for receiving the multi-axis pivotal couplers 49 such that the multi-axis pivotal couplers 49 are positioned about a distal end 66 of a bone 5.

The plurality of connecting members 13 includes a standard connector 67. The standard connector 67 comprises two connecting portions 68. Each of the connecting portions 68 is designed for receiving the connecting bars 9. The connecting portions 68 are pivotally coupled and have a securing member 36. The securing member 36 is designed for selectively coupling the connecting bars 9 to the connecting portions 68 such that the standard connector 67 is designed for selectively coupling two connecting bars 9 for the purpose of forming the frame assembly 1.

The plurality of connecting members 13 includes an offset connector 69. The offset connector 69 comprises two end members 70 and a plurality of inner members 71. All of the inner members 71 are pivotally coupled together thereby forming a chainlike design such that the inner members 71 are designed for allowing the end members 70 to be offset.

The end members 70 are selectively couplable to ends 72 of two different connecting bars 9. The offset connector 69 is designed for allowing two connecting bars 9 to be selectively coupled along a common longitudinal axis but with an offset perpendicular to the longitudinal axis as required when forming the frame assembly 1.

Each of the end members 70 has a plurality of securing members 36. The securing members 36 are positioned on opposing side surfaces 73 of the end members 70. The securing members 36 are designed for selectively coupling the end members 70 to ends 72 of the connecting bars 9.

The plurality of connecting members 13 includes an angular connector 74. The angular connector 74 includes a main bracket member 75. The main bracket member 75 comprises two outer portions 76 and a central portion 77. Each of the outer portions 76 is deflected equilaterally from a longitudinal axis of the central portion 77 of the angular connector 74.

Each of the portions 76, 77 includes a coupling member 78. The coupling member 78 comprises a shaft section 79. The shaft sections 79 are pivotally coupled to the portions 76, 77 of the angular connector 74. Each of the portions 76, 77 includes a securing member 36 such that the angular connector 74 is designed for selectively coupling a plurality of the connecting bars 9 along a longitudinal axis of the connecting bars 9 in the formation of the frame assembly 1.

The plurality of connecting members 13 includes a semi-circular connector 61. The semi-circular connector 61 is designed to be simultaneously coupled to a connecting bar 9 and a semi-circular connecting bar 12.

All of said components comprise an aluminum titanium steel alloy material.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A universal modular component external fixation system for immobilizing bone fragments in long bone fractures, the universal modular component external fixation system comprising:

a frame assembly, said frame assembly having a plurality of pins, said pins comprising a plurality of fixation pins and compression pins, said pins being adapted for being threadably couplable to a bone for the purpose of rendering the bone immobile;

said frame assembly including a plurality of couplers, said couplers comprising a pin section and a bar section, said pin section being selectively couplable to said pins such that said pin section is adapted for holding said pins in a fixed position relative to said frame assembly;

said frame assembly including a plurality of connecting bars, said connecting bars comprising straight connecting bars and semi-circular connecting bars, said connecting bars being slidable through said bar section of said couplers, said connecting bars being adapted for positioning said couplers along said connecting bars such that said couplers are selectively couplable to said pins when said pins are positioned in the bones;

said frame assembly including a plurality of connecting members, said connecting members being selectively couplable to said connecting bars, said connecting members being adapted for rigidly securing a plurality of said connecting bars together thereby completely immobilizing all of said pins coupled to the bone fragments for the duration of the healing process;

said plurality of fixation pins of said frame assembly comprising a standard fixation pin and a step down fixation pin, each of said fixation pins having a threaded portion, said threaded portion of said fixation pins being located proximate a point end of said fixation pins, said threaded portion being adapted for being screwed into the bone;

each of said fixation pins having a tool end, said tool end being adapted for allowing the user to utilize a tool to turn said fixation pin for the purpose of inserting or extracting said fixation pin to and from the bone; and each of said fixation pins having a coupling portion and an insertion portion, said coupling portions of said fixation pins having equal diameters, a diameter of said coupling portion of said standard fixation pin being equal to a diameter of said insertion portion of said standard fixation pin, whereas a diameter of said insertion portion of said step down fixation pin is less than a diameter of said coupling portion of said step down fixation pin thereby making fixation pins have different insertion diameters both selectively couplable to one of said couplers; and said compression pin of said frame assembly being a substantially elongate tubular member, said compression pin having said threaded portion and said coupling portion, said compression pin having a tool portion, said tool portion being positioned proximate a medial portion of said compression pin such that the associated one of said couplers is positioned between said tool portion and a free end of said compression pin, said tool portion being adapted for allowing the user to utilize a tool to turn said compression pin for the purpose of inserting or extracting said compression pin from the bone.

2. The universal modular component external fixation system as set forth in claim 1, further comprising:

said compression pin having a head portion, said head portion being located adjacent said tool portion, said head portion being adapted for abutting an outer surface of the fractured bone when said threaded portion of said compression pin passes completely through a first part of a fractured bone and is securely coupled to a second part of the fractured bone such that said compression pin is adapted for biasing the first and second parts of the bone together until properly healed.

3. The universal modular component external fixation system as set forth in claim 2, further comprising:

said compression pin including a guide wire, said guide wire being insertable into said compression pin such that said guide wire protrudes outwardly from said point end of said compression pin, said guide wire being positioned in the bone prior to screwing in said compression pin such that said guide wire is adapted for predetermining a desired angle and location of said compression pin by viewing x-rays with said guide wire inserted thereby assuring proper placement of said compression pin in the fractured bone.

4. The universal modular component external fixation system as set forth in claim 3, further comprising:

a plurality of said compression pins comprising a plurality of lengths of said insertion portions for the purpose of matching a particular compression pin to a specific bone fracture requirement.

5. The universal modular component external fixation system as set forth in claim 1, further comprising:

said frame assembly including a drill guide assembly, said drill guide assembly comprising a guide holder, a plurality of drill guides, and a trocar, said trocar being insertable into said guide holder such that said trocar protrudes outwardly from a bottom end of said guide holder thereby puncturing muscle matter covering the bone, one of said plurality of drill guides then being inserted into said guide holder after said trocar is removed such that said drill guides is adapted for guiding various sized drill bits to ensure the uniformity of said hole being drilled into the bone thereby assuring proper placement of said fixation pins.

6. The universal modular component external fixation system as set forth in claim 1, further comprising:

said plurality of said couplers of said frame assembly including a multi-pin fixed coupler, said bar section of said multi-pin fixed coupler having a plurality of securing members, said securing members being positioned on a bar end of said multi-pin fixed coupler, said securing members being adapted for contacting said connecting bar thereby allowing a user to selectively fixate said multi-pin fixed coupler onto said connecting bar in a desired position.

7. The universal modular component external fixation system as set forth in claim 6, further comprising:

said pin section of said multi-pin fixed coupler having a plurality of fixation pin apertures, said apertures being formed by sectional portions of said pin section of said multi-pin fixed coupler, a diameter of said fixation pins being greater than a diameter of said apertures such that said fixation pins are insertable into said apertures when said sectional portions are parted, said apertures being adapted for securing said fixation pins when a plurality of said securing members of said pin section are biased inwardly thus forcing said sectional portions together such that the diameter of said apertures decreases thereby securing said fixation pins to said pin section of said multi-pin fixed coupler.

8. The universal modular component external fixation system as set forth in claim 7, further comprising:

said frame assembly including a plurality of said multi-pin fixed couplers, each of said multi-pin fixed couplers having a different number of pin apertures, said apertures being aligned substantially parallel to said connecting bars thereby allowing the user to space said fixation pins as needed along the fractured bone for the purpose of immobilizing particular parts of the fractured bone for proper healing of the fracture.

9. The universal modular component external fixation system as set forth in claim 6, further comprising:

said plurality of said couplers of said frame assembly including a single axis pivotal coupler, said pin section of said single axis pivotal coupler having a pivotal pin member, said pivotal pin member having a bore therethrough, said bore being adapted for receiving one of said fixation pins, said pivotal pin member being positioned within said pin section of said single axis pivotal coupler; and said pivotal pin member being pivotable thirty degrees either side of a central axis in a plane parallel to a vertical plane of a longitudinal axis of said connecting bars wherein the central axis is substantially perpendicular to the longitudinal axis of said connecting bars thereby allowing the user to position said fixation pin at various angles with respect to said connecting bars as needed.

10. The universal modular component external fixation system as set forth in claim 9, further comprising:

a clamping member of said pin section being biased inwardly contacting said pivotal pin member thereby securing said pivotal pin member in a fixed position; and said pivotal pin member of said single axis pivotal coupler being collapsible when said clamping member secures said pivotal pin member such that a diameter of said bore of said pivotal pin member is decreased upon the securing of said pivotal pin member by said clamping member maintaining a position of one of said pins in said bore.

11. The universal modular component external fixation system as set forth in claim 9, further comprising:

upper and lower surfaces of said pin section of said single axis pivotal coupler having an inner edge portion, said inner edge portion being beveled outwardly from an outer surface of said pivotal pin member thereby allowing said fixation pin to fully pivot the designated angular range of said pivotal pin member.

12. The universal modular component external fixation system as set forth in claim 11, further comprising:

said bar section of said single axis pivotal coupler having a securing member such that said bar section is adapted for being selectively couplable to one of said connecting bars.

13. The universal modular component external fixation system as set forth in claim 1, further comprising:

said plurality of said couplers of said frame assembly including a multi-axis pivotal coupler, said pin section of said multi-axis pivotal coupler having a multi-axis pin member, said multi-axis pin member having a bore throughout, said bore being adapted for receiving one of said pins, said multi-axis pin member being positioned within said pin section of said multi-axis pivotal coupler, said multi-axis pin member being pivotable thirty degrees about a central axis wherein the central axis is substantially perpendicular to a longitudinal axis of said connecting bars thereby allowing the user to position said pins at various angles with respect to said connecting bars as required.

14. The universal modular component external fixation system as set forth in claim 13, further comprising:

a clamping member of said pin section being biased inwardly contacting said multi-axis pin member thereby securing said multi-axis pin member in a fixed position; and said multi-axis pin member of said multi-axis pivotal coupler being collapsible when said clamping member secures said pivotal pin member such that a diameter of said bore of said multi-axis pin member is decreased upon the securing of said multi-axis pin member by said clamping member thereby maintaining a position of one of said pins in said bore.

15. The universal modular component external fixation system as set forth in claim 14, further comprising:

upper and lower surfaces of said pin section of said multi-axis pivotal coupler having an inner edge portion, said inner edge portion being beveled outwardly from an outer surface of said multi-axis pin member thereby allowing said fixation pin to fully pivot the designated angular range of said multi-axis pin member.

16. The universal modular component external fixation system as set forth in claim 15, further comprising:

said bar section of said multi-axis pivotal coupler being adapted for receiving said semi-circular connecting bars, said bar section having a securing member such that said bar section is adapted for being selectively couplable to one of said semi-circular connecting bars.

17. The universal modular component external fixation system as set forth in claim 13, further comprising:

said semi-circular connecting bars comprising a straight portion and a curved portion, said portions being fixedly coupled such that a plane in which said curved portion lies is substantially perpendicular to a longitudinal axis of said straight portion; and said semi-circular connecting bars having a plurality of different length straight portions in conjunction with a plurality of curved portions having different radii, said curved portions of said semi-circular connecting bars being adapted for receiving said multi-axis pivotal couplers such that said multi-axis pivotal couplers are positioned about a distal end of a bone.

18. The universal modular component external fixation system as set forth in claim 1, further comprising:

said plurality of said couplers of said frame assembly including a traction/distraction coupler, said pin section of said traction/distraction coupler having a plurality of pin receiving holes, said receiving holes being aligned along a longitudinal axis of said connecting bar when said connecting bar is received by said bar section of said traction/distraction coupler; and said pin section having a plurality of securing members such that said pins is selectively couplable to said pin section when said securing members are biased inwardly towards said pins.

19. The universal modular component external fixation system as set forth in claim 18, further comprising:

said bar section of said traction/distraction coupler having a traction/distraction member, said traction/distraction member being positioned proximate a middle section of said traction/distraction coupler, said traction/distraction member being threadably couplable to a threaded connecting bar, said traction/distraction member being rotatable about the longitudinal axis of said threaded connecting bar such that rotation of said traction/distraction member biases said traction/distraction coupler longitudinally along said threaded connecting bar; and said bar section of said traction/distraction coupler having a securing member, said securing member being adapted for contacting said threaded rod for the purpose of preventing rotation with respect to said traction/distraction coupler such that a pair of traction/distraction couplers are coupled to said threaded rod being utilized to bias bones on either side of the fracture as required when a first of said traction/distraction couplers is secured to said threaded rod and a second of said traction/distraction couplers is biased along said threaded rod by rotation of said traction/distraction member when said pins are secured to either side of the fracture.

20. The universal modular component external fixation system as set forth in claim 1, further comprising:

all of said couplers having smooth surfaces and beveled edged thereby allowing a user to grasp said couplers when the user is wearing latex gloves and has a substantial amount of blood and fluids on the glove making the gloves slippery.

21. The universal modular component external fixation system as set forth in claim 1, further comprising:

said straight connecting bars of said connecting bars including standard connecting bars and threaded connecting bars, said standard connecting bars comprising smooth tubular members of various predetermined lengths, said standard connecting bars being adapted for receiving said couplers; and said threaded connecting bars comprising threaded tubular members of various predetermined lengths, said threaded connecting bars being adapted for receiving a plurality of traction/distraction couplers.

22. The universal modular component external fixation system as set forth in claim 1, further comprising:

said plurality of connecting members including a standard connecting member, said standard connecting member comprising two connecting portions, each of said connecting portions being adapted for receiving said connecting bars, said connecting portions being pivotally coupled, said standard connecting member having a clamping member, said clamping member being adapted for selectively coupling said connecting bars to said connecting portions such that said standard connecting member is adapted for selectively coupling two connecting bars for the purpose of forming said frame assembly.

23. The universal modular component external fixation system as set forth in claim 1, further comprising:

said plurality of connecting members including an offset connector, said offset connector comprising two end members and a plurality of inner members, all of said inner members being pivotally coupled together thereby forming a chainlike design such that said inner members are adapted for allowing said end members to be offset; and said end members adapted for selectively coupling to distal ends of two different connecting bars such that said offset connector is adapted for allowing two connecting bars to be selectively coupled along a common longitudinal axis but with an offset perpendicular to said longitudinal axis as required when forming said frame assembly.

24. The universal modular component external fixation system as set forth in claim 23, further comprising:

each of said end members having a plurality of securing members, said securing members positioned on opposing side surfaces of said end members, said securing members adapted for selectively coupling said end members to ends of said connecting bars.

25. The universal modular component external fixation system as set forth in claim 1, further comprising:

said plurality of connecting members including an angular connector, said angular connector including a main bracket member, said main bracket member comprising two outer portions and a central portion, each of said outer portions deflected equilaterally from a longitudinal axis of said central portion of said angular connector; and each of said portions including a coupling member, said coupling member comprising a shaft section, said shaft sections pivotally coupled to said portions of said angular connector, each of said portions including a securing member such that said angular connector is adapted for selectively coupling a plurality of said connecting bars along a longitudinal axis of said connecting bars in the formation of said frame assembly.

26. The universal modular component external fixation system as set forth in claim 1, further comprising:

said plurality of connecting members includes a semi-circular connector, said semi-circular connector being adapted for being simultaneously coupled to said connecting bar and said semi-circular connecting bar.

27. The universal modular component external fixation system as set forth in claim 1, further comprising:

all of said components comprising an aluminum titanium steel alloy material.

28. A universal modular component external fixation system for immobilizing bone fragments in long bone fractures, the universal modular component external fixation system comprising:

a frame assembly, said frame assembly having a plurality of pins, said pins comprising a plurality of fixation pins and compression pins, said pins being adapted for being threadably couplable to a bone for the purpose of rendering the bone immobile;

said frame assembly including a plurality of couplers, said couplers comprising a pin section and a bar section, said pin section being selectively couplable to said pins such that said pin section is adapted for holding said pins in a fixed position relative to said frame assembly;

said frame assembly including a plurality of connecting bars, said connecting bars comprising straight connecting bars and semi-circular connecting bars, said connecting bars being slidable through said bar section of said couplers, said connecting bars adapted for positioning said couplers along said connecting bars such that said couplers are selectively couplable to said pins when said pins are positioned in the bones;

said frame assembly including a plurality of connecting members, said connecting members selectively couplable to said connecting bars, said connecting members adapted for rigidly securing a plurality of said connecting bars together thereby completely immobilizing all of said pins coupled to the bone fragments for the duration of the healing process;

said plurality of fixation pins of said frame assembly comprising a standard fixation pin and a step down fixation pin, each of said fixation pins having a threaded portion, said threaded portion of said fixation pins being located proximate a point end of said fixation pins, said threaded portion being adapted for screwed into the bone;

each of said fixation pins having a tool end, said tool end adapted for allowing the user to utilize a tool to turn said fixation pin for the purpose of inserting or extracting said fixation pin to and from the bone;

each of said fixation pins having a coupling portion and an insertion portion, said coupling portions of said fixation pins having equal diameters, a diameter of said coupling portion of said standard fixation pin being equal to a diameter of said insertion portion of said standard fixation pin being whereas a diameter of said insertion portion of said step down fixation pin is less than a diameter of said coupling portion of said step down fixation pin thereby making fixation pins have different insertion diameters both selectively couplable to one of said couplers;

said compression pin of said frame assembly a substantially elongate tubular member, said compression pin having said threaded portion and said coupling portion, said compression pin having a tool portion, said tool portion positioned proximate a medial portion of said compression pin, said tool portion adapted for allowing the user to utilize a tool to turn said compression pin for the purpose of inserting or extracting said compression pin from the bone;

said compression pin having a head portion, said head portion located adjacent said tool portion, said head portion adapted for abutting an outer surface of the fractured bone when said threaded portion of said compression pin passes completely through a first part of a fractured bone and is securely coupled to a second part of the fractured bone such that said compression pin is adapted for biasing the first and second parts of the bone together until properly healed;

said compression pin including a guide wire, said guide wire being insertable into said compression pin such that said guide wire protrudes outwardly from said point end of said compression pin, said guide wire being positioned in the bone prior to screwing in said compression pin such that said guide wire is adapted for predetermining a desired angle and location of said compression pin by viewing x-rays with said guide wire inserted thereby assuring proper placement of said compression pin in the fractured bone;

a plurality of said compression pins comprising a plurality of lengths of said insertion portions for the purpose of matching a particular compression pin to a specific bone fracture requirement;

said frame assembly including a drill guide assembly, said drill guide assembly comprising a guide holder, a plurality of drill guides, and a trocar, said trocar being insertable into said guide holder such that said trocar protrudes outwardly from a bottom end of said guide holder thereby puncturing muscle matter covering the bone, one of said plurality of drill guides then inserted into said guide holder after said trocar being removed such that said drill guides is adapted for guiding various sized drill bits to ensure the uniformity of said hole drilled into the bone thereby assuring proper placement of said fixation pins;

said plurality of said couplers of said frame assembly including a multi-pin fixed coupler, said bar section of said multi-pin fixed coupler having a plurality of securing members, said securing members positioned on a bar end of said multi-pin fixed coupler, said securing members being adapted for contacting said connecting bar thereby allowing a user to selectively fixate said multi-pin fixed coupler onto said connecting bar in a desired position;

said pin section of said multi-pin fixed coupler having a plurality of fixation pin apertures, said apertures formed by sectional portions of said pin section of said multi-pin fixed coupler, a diameter of said fixation pins being greater than a diameter of said apertures such that said fixation pins are insertable into said apertures when said sectional portions are parted, said apertures being adapted for securing said fixation pins when a plurality of said securing members of said pin section are biased inwardly thus forcing said sectional portions together such that the diameter of said apertures decreases thereby securing said fixation pins to said pin section of said multi-pin fixed coupler;

said frame assembly including a plurality of said multi-pin fixed couplers, each of said multi-pin fixed couplers having a different number of pin apertures, said apertures being aligned substantially parallel to said connecting bars thereby allowing the user to space said fixation pins as needed along the fractured bone for the purpose of immobilizing particular parts of the fractured bone for proper healing of the fracture;

said plurality of said couplers of said frame assembly including a single axis pivotal coupler, said pin section of said single axis pivotal coupler having a pivotal pin member, said pivotal pin member having a bore therethrough, said bore being adapted for receiving one of said fixation pins, said pivotal pin member being positioned within said pin section of said single axis pivotal coupler;

said pivotal pin member being pivotable thirty degrees either side of a central axis in a plane parallel to a vertical plane of a longitudinal axis of said connecting bars wherein the central axis is substantially perpendicular to the longitudinal axis of said connecting bars thereby allowing the user to position said fixation pin at various angles with respect to said connecting bars as needed;

a clamping member of said pin section being biased inwardly contacting said pivotal pin member thereby securing said pivotal pin member in a fixed position;

said pivotal pin member of said single axis pivotal coupler being collapsible when said clamping member secures said pivotal pin member such that a diameter of said bore of said pivotal pin member being decreased upon the securing of said pivotal pin member by said clamping member maintaining a position of one of said pins in said bore;

upper and lower surfaces of said pin section of said single axis pivotal coupler having an inner edge portion, said inner edge portion being beveled outwardly from an outer surface of said pivotal pin member thereby allowing said fixation pin to fully pivot the designated angular range of said pivotal pin member;

said bar section of said single axis pivotal coupler having a securing member such that said bar section is adapted for selectively couplable to one of said connecting bars;

said plurality of said couplers of said frame assembly including a multi-axis pivotal coupler, said pin section of said multi-axis pivotal coupler having a multi-axis pin member, said multi-axis pin member having a bore throughout, said bore adapted for receiving one of said pins, said multi-axis pin member being positioned within said pin section of said multi-axis pivotal coupler, said multi-axis pin member being pivotable thirty degrees about a central axis wherein the central axis is substantially perpendicular to a longitudinal axis of said connecting bars thereby allowing the user to position said pins at various angles with respect to said connecting bars as required;

a clamping member of said pin section being biased inwardly contacting said multi-axis pin member thereby securing said multi-axis pin member in a fixed position;

said multi-axis pin member of said multi-axis pivotal coupler being collapsible when said clamping member secures said pivotal pin member such that a diameter of said bore of said multi-axis pin member is decreased upon the securing of said multi-axis pin member by said clamping member thereby maintaining a position of one of said pins in said bore;

upper and lower surfaces of said pin section of said multi-axis pivotal coupler having an inner edge portion, said inner edge portion being beveled outwardly from an outer surface of said multi-axis pin member thereby allowing said fixation pin to fully pivot the designated angular range of said multi-axis pin member;

said bar section of said multi-axis pivotal coupler being adapted for receiving said semi-circular connecting bars, said bar section having a securing member such that said bar section is adapted for being selectively couplable to one of said semi-circular connecting bars;

said plurality of said couplers of said frame assembly including a traction/distraction coupler, said pin section of said traction/distraction coupler having a plurality of pin receiving holes, said receiving holes aligned along a longitudinal axis of said connecting bar when said connecting bar is received by said bar section of said traction/distraction coupler;

said pin section having a plurality of securing members such that said pins is selectively couplable to said pin section when said securing members are biased inwardly towards said pins;

said bar section of said traction/distraction coupler having a traction/distraction member, said traction/distraction member being positioned proximate a middle section of said traction/distraction coupler, said traction/distraction member being threadably couplable to a threaded connecting bar, said traction/distraction member being rotatable about the longitudinal axis of said threaded connecting bar such that rotation of said traction/distraction member biases said traction/distraction coupler longitudinally along said threaded connecting bar;

said bar section of said traction/distraction coupler having a securing member, said securing member being adapted for contacting said threaded rod for the purpose of preventing rotation with respect to said traction/distraction coupler such that a pair of traction/distraction couplers are coupled to said threaded rod being utilized to bias bones on either side of the fracture as required when a first of said traction/distraction couplers is secured to said threaded rod and a second of said traction/distraction couplers is biased along said threaded rod by rotation of said traction/distraction member when said pins are secured to either side of the fracture;

all of said couplers having smooth surfaces and beveled edged thereby allowing a user to grasp said couplers when the user is wearing latex gloves and has a substantial amount of blood and fluids on the glove making the gloves slippery;

said straight connecting bars of said connecting bars including standard connecting bars and threaded connecting bars, said standard connecting bars comprising smooth tubular members of various predetermined lengths, said standard connecting bars adapted for receiving said couplers;

said threaded connecting bars comprising threaded tubular members of various predetermined lengths, said threaded connecting bars being adapted for receiving a plurality of traction/distraction couplers;

said semi-circular connecting bars comprising a straight portion and a curved portion, said portions being fixedly coupled such that a plane in which said curved portion lies is substantially perpendicular to a longitudinal axis of said straight portion;

said semi-circular connecting bars having a plurality of different length straight portions in conjunction with a plurality of curved portions having different radii, said curved portions of said semi-circular connecting bars adapted for receiving said multi-axis pivotal couplers such that said multi-axis pivotal couplers are positioned about a distal end of a bone;

said plurality of connecting members including a standard connecting member, said standard connecting member comprising two connecting portions, each of said connecting portions being adapted for receiving said connecting bars, said connecting portions being pivotally coupled, said standard connecting member having a clamping member, said clamping member being adapted for selectively coupling said connecting bars to said connecting portions such that said standard connecting member is adapted for selectively coupling two connecting bars for the purpose of forming said frame assembly;

said plurality of connecting members including an offset connector, said offset connector comprising two end members and a plurality of inner members, all of said inner members being pivotally coupled together thereby forming a chainlike design such that said inner members are adapted for allowing said end members to be offset;

said end members being adapted for selectively coupling to distal ends of two different connecting bars such that said offset connector is adapted for allowing two connecting bars to be selectively coupled along a common longitudinal axis but with an offset perpendicular to said longitudinal axis as required when forming said frame assembly;

each of said end members having a plurality of securing members, said securing members positioned on opposing side surfaces of said end members, said securing members being adapted for selectively coupling said end members to ends of said connecting bars;

said plurality of connecting members including an angular connector, said angular connector including a main bracket member, said main bracket member comprising two outer portions and a central portion, each of said outer portions being deflected being equilaterally from a longitudinal axis of said central portion of said angular connector;

each of said portions including a coupling member, said coupling member comprising a shaft section, said shaft sections being pivotally coupled to said portions of said angular connector, each of said portions including a securing member such that said angular connector is adapted for selectively coupling a plurality of said connecting bars along a longitudinal axis of said connecting bars in the formation of said frame assembly;

said plurality of connecting members includes a semi-circular connector, said semi-circular connector being adapted for being simultaneously coupled to said connecting bar and said semi-circular connecting bar;

all of said components comprising an aluminum titanium steel alloy material.

* * * * *